US006755350B2

(12) United States Patent
Rochford et al.

(10) Patent No.: US 6,755,350 B2
(45) Date of Patent: Jun. 29, 2004

(54) SENSUAL LABEL

(75) Inventors: William T. Rochford, Rochester, NY (US); Robert P. Bourdelais, Pittsford, NY (US); Mridula Nair, Penfield, NY (US)

(73) Assignee: Eastman Kodak Company, Rochester, NY (US)

(*) Notice: Subject to any disclaimer, the term of this patent is extended or adjusted under 35 U.S.C. 154(b) by 253 days.

(21) Appl. No.: 10/027,975

(22) Filed: Dec. 21, 2001

(65) Prior Publication Data

US 2003/0122371 A1 Jul. 3, 2003

(51) Int. Cl.[7] .......................... A24F 25/00; A61L 9/04; B41M 5/025; B23B 3/26

(52) U.S. Cl. .......................... 239/34; 239/54; 428/905; 428/41.7; 428/321.1; 428/321.5

(58) Field of Search ............................ 239/56, 34, 54; 428/201, 41.7, 41.8, 43, 154, 317.5, 321.5, 321.1, 905

(56) References Cited

U.S. PATENT DOCUMENTS

| | | | | | |
|---|---|---|---|---|---|
| 3,685,734 | A | * | 8/1972 | Paciorek et al. | 239/56 |
| 4,493,869 | A | * | 1/1985 | Sweeny et al. | 428/201 |
| 4,528,226 | A | * | 7/1985 | Sweeny | 428/40.2 |
| 4,606,956 | A | * | 8/1986 | Charbonneau et al. | 428/40.2 |
| 4,769,264 | A | * | 9/1988 | Dreger | 428/40.2 |
| 5,114,735 | A | * | 5/1992 | Rua et al. | 427/7 |
| 5,318,327 | A | | 6/1994 | Daneshvar | |
| 5,398,070 | A | | 3/1995 | Lee | |
| 5,439,172 | A | * | 8/1995 | Comyn et al. | 239/34 |
| 5,566,693 | A | * | 10/1996 | Gunderman et al. | 132/333 |
| 5,640,931 | A | * | 6/1997 | Markham | 119/711 |
| 5,888,683 | A | | 3/1999 | Gula et al. | |
| 5,891,825 | A | | 4/1999 | Ushio et al. | |
| 5,970,300 | A | | 10/1999 | Acquaviva | |
| 5,985,075 | A | | 11/1999 | Freedman | |
| 5,995,770 | A | | 11/1999 | Rochford et al. | |
| 6,022,679 | A | | 2/2000 | Kawamoto | |
| 6,110,552 | A | | 8/2000 | Casey et al. | |
| 6,130,024 | A | | 10/2000 | Aylward et al. | |
| 6,146,744 | A | | 11/2000 | Freedman | |
| 6,248,377 | B1 | * | 6/2001 | Levine | 426/87 |
| 6,277,547 | B1 | | 8/2001 | Bourdelais et al. | |

FOREIGN PATENT DOCUMENTS

| | | |
|---|---|---|
| WO | WO 93/08676 | 5/1993 |
| WO | WO 94/26375 | 11/1994 |

OTHER PUBLICATIONS

U.S. patent application Ser. No. 10/037,050, filed Dec. 21, 2001, Photographic Member With Flexibilizer Material.
U.S. patent application Ser. No. 10/028,865, filed Dec. 21, 2001, Balanced Architecture for Adhesive Image Media.
U.S. patent application Ser. No. 10/029,050, filed Dec. 21, 2001, Expansion of Color Gamut for Silver Halide Media.
U.S. patent application Ser. No. 10/027,971, filed Dec. 21, 2001, Quintessential Pictorial Label and its Distribution.
U.S. patent application Ser. No. 10/027,974, filed Dec. 21, 2001, Protective Layer for Hydrophilic Packaging Material.
U.S. patent application Ser. No. 10/027,582, filed Dec. 21, 2001, Label With Curl and Moisture Resistant Protective Layer.
U.S. patent application Ser. No. 10/027,512, filed Dec. 21, 2001, Photographic Label for Reproduction of Fine Print.
U.S. patent application Ser. No. 10/037,953, filed Dec. 21, 2001, Transparent Label With Enhanced Sharpness.

* cited by examiner

*Primary Examiner*—William C. Doerrler
(74) *Attorney, Agent, or Firm*—Paul A. Leipold

(57) ABSTRACT

The invention relates to a sensual pressure sensitive adhesive label comprising an image having at least one overcoat layer over said image wherein said overcoat layer comprises comprising at least one tactile or olfactory feature

53 Claims, No Drawings

SENSUAL LABEL

FIELD OF THE INVENTION

The invention relates to packaging materials. In a preferred form it relates to the use of both silver halide and ink printing for the printing of text, graphics and images applied to a scented packaging material.

BACKGROUND OF THE INVENTION

Pressure sensitive labels applied are applied to packages to build brand awareness, show the contents of the package, convey a quality message regarding the contents of a package and supply consumer information such as directions on product use, or an ingredient listing of the contents. Printing on the pressure sensitive label is typically applied directly to the package or a printed media, typically printed using gravure printing or flexography is applied to the package. The three types of information applied to a pressure sensitive label are text, graphic and images. Some packages only require one type of information while other packages require more than one type of information.

Prior art labels that are applied to packages consist of a base material, a pressure sensitive adhesive and a liner. The label substrate consisting of the base, pressure sensitive adhesive and liner are typically laminated and then printed utilizing a variety of non photographic printing methods. After printing, the labels are generally protected by an over laminate material or a protective coating. The completed label consisting of a protection layer, printed information, base and pressure sensitive adhesive and liner material is applied to packages utilizing high speed labeling equipment.

Prior art labels typically comprise visual content such as graphics, texts and images. Recent product labels also contain facestock materials that are eye catching. Examples include microembossed polyester films, clear labels and nacreous pigmented inks. There is a continuing need for further improving the quality of the image and there is a continuing need for improving the advertising power of labels.

Flexography is an offset letterpress technique where the printing plates are made from rubber or photopolymers. The printing on pressure sensitive label is accomplished by the transfer of ink from the raised surface of the printing plate to the surface of the material being printed. The rotogravure method of printing uses a print cylinder with thousands of tiny cells which are below the surface of the printing cylinder. The ink is transferred from the cells when the print cylinder is brought into contact with the pressure sensitive label at the impression roll. Printing inks for flexography or rotogravure include solvent based inks, water based inks and radiation cured inks. While rotogravure and flexography printing do provide acceptable image quality, these two printing methods require expensive and time consuming preparation of print cylinders or printing plates which make printing jobs of less than 100,000 units expensive as the set up cost and the cost of the cylinders or printing plates is typically depreciated over the size of the print job.

Recently, digital printing has become a viable method for the printing of information on packages. The term digital printing refers to the electronic digital characters or electronic digital images that can be printed by an electronic output device capable of translating digital information. The two main digital printing technologies are ink jet and electrophotography.

The introduction of piezo impulse drop-on-demand (DOD) and thermal DOD ink jet printers in the early 1980's provided ink jet printing systems. These early printers were very slow, and the ink jet nozzles often clogged. In the 1990's Hewlett Packard introduced the first monochrome ink jet printer, and, shortly thereafter, the introduction of color, wide format ink jet printers enabled businesses to enter the graphic arts market. Today, a number of different ink jet technologies are being used for packaging, desktop, industrial, commercial, photographic, and textile applications.

In piezo technology, a piezo crystal is electrically stimulated to create pressure waves, which eject ink from the ink chamber. The ink can be electrically charged and deflected in a potential field, allowing the different characters to be created. More recent developments have introduced DOD multiple jets that utilize conductive piezo ceramic material, which, when charged, increases the pressure in the channel and forces a drop of ink from the end of the nozzle. This allows for very small droplets of ink to form and be delivered at high speed at very high resolution, approximately 1,000 dpi printing.

Until recently, the use of color pigments in jet inks was uncommon. However, this is changing rapidly. Submicron pigments were developed in Japan for ink jet applications. Use of pigments allows for more temperature resistant inks required for thermal ink jet printers and laminations. Pigmented water-based jet inks are commercially available, and UV-curable jet inks are in development. Pigmented inks have greater lightfastness and water-resistance.

Digital ink jet printing has the potential to revolutionize the printing industry by making short-run, color print jobs more economical. However, the next commercial stage will require significant improvements in ink jet technology; the major hurdle remaining is to improve print speed. Part of this problem is the limitation of the amount of data the printer can handle rapidly. The more complex the design, the slower the printing process. Right now they are about 10 times slower than comparable digital electrostatic printers.

Electrophotography was invented in the 1930's by Chester Carlson. By the early 1970's, the development of an electrophotographic color copier was being investigated by many companies. The technology for producing color copiers was already in place, but the market was not. It would take many more years until customer demand for color copies would create the necessary incentive to develop suitable electrostatic color copiers. By the late 1970's a few companies were using fax machines that could scan a document, reduce the images to electronic signals, send them out over the telephone wire, and, using another fax machine, retrieve the electronic signals and print the original image using heat-sensitive papers to produce a printed copy.

In 1993 Indigo and Xeikon introduced commercial digital printing machines targeted on short-run markets that were dominated by sheet-fed lithographic printers. Elimination of intermediate steps associated with negatives and plates used in offset printing provides faster turnaround and better customer service. These digital presses share some of the characteristics of traditional xerography but use very specialized inks. Unlike inks for conventional photocopiers, these inks are made with very small particle size components in the range of 1 μm. Dry toners used in xerography are typically 8–10 μm in size.

In 1995 Indigo introduced the Ominus press designed for printing flexible packaging products. The Ominus uses a digital offset color process called One Shot Color that has six colors. A key improvement has been the use of a special white Electro ink for transparent substrates. The Ominus web-fed digital printing system allows printing of various substrates using an offset cylinder that transfers the color image to the substrate. In principle, this allows perfect register regardless of the substrate being printed; paper, film, and metal can be printed by this process. This digital printing system is based on an electrophotographic process where the electrostatic image is created on the surface of a photoconductor by first charging the photo-conductor by charge corona and exposing the photoconductive surface to a light source in image fashion.

The charged electrostatic latent image is then developed using ink containing an opposite charge to that on the image. This part of the process is similar to that of electrostatic toners associated with photo-copying machines. The latent charged electrostatic image formed on the photoconductor surface is developed by means of electrophoretic transfer of the liquid toner. This electrostatic toner image is then transferred to a hot blanket, which coalesces the toner and maintains it in a tacky state until it is transferred to the substrate, which cools the ink and produces a tack-free print.

Electro inks typically comprise mineral oil and volatile organic compounds below that of conventional offset printing inks. They are designed so that the thermoplastic resin will fuse at elevated temperatures. In the actual printing process, the resin coalesced, the inks are transferred to the substrate, and there is no need to heat the ink to dry it. The ink is deposited on the substrate essentially dry, although it becomes tack-free as it cools and reaches room temperature.

For several decades a magnetic digital technology called "magnetography" has been under development. This process involves creating electrical images on a magnetic cylinder and using magnetic toners as inks to create the image. The potential advantage of this technology lies in its high press speed. Tests have shown speeds of 200 meters per minute. Although these magnetic digital printers are limited to black and white copy, developments of color magnetic inks would make this high-speed digital technology economically feasible. The key to its growth will be further development of the VHSM (very high speed magnetic) drum and the color magnetic inks.

Within the magnetic digital arena, a hybrid system called magnetolithography has been built and tested on narrow web and short-run applications developed by Nipson Printing Systems in Belfort, France. The technology appears to provide high resolution, and tests have been conducted using a silicon-based, high density, magnetographic head. Much more work is necessary in the ink development to bring this system to a competitive position relative to ink jet or electrophotography. However, the fact that it has high speed printing potential makes it an attractive alternate for packaging applications in which today's ink jet and electrophotography technologies are lagging.

Photographic materials have been known for use as prints for preserving memories for special events such as birthdays and vacations. They also have been utilized for large display materials utilized in advertising. These materials have been known as high quality products that are costly and somewhat delicate as they would be easily defaced by abrasion, water, or bending. Photographs are traditionally placed in frames, photo albums, and behind protective materials in view of their fragile and delicate nature, as well as their value. They are considered luxury items for the consumers to preserve a record of important events in their lives. They also have been considered as expensive display materials for advertising. In view of their status as luxury items, they have not been utilized in other areas of commerce.

The use of scents with media (images and text) is a very familiar marketing tool. Magazines have been using scents to entice customers by enabling sampling or by association of the scent with a product for many years. The use of other sensory stimuli such as tactile is also used to promote products. For example, free samples of items such as skin care products and soaps are given away to customers in order to promote specific attributes including sensory features. A free sample of a "non-greasy" lotion enables the users to experience sensory stimuli directly. The sensory stimuli are product features used businesses to support product differentiation strategies as well as to strengthen and build brand recognition.

Intellectual property around the use of scents and images has been developed to support business strategies. U.S. Pat. No. 5,318,327 provides for a card that has a scent-receiving zone and a greeting message receiving zone. WO 93/08676 and WO 94/26375 each disclose a device for intensifying or increasing sensorial perception of visual and/or acoustic representations in, for example, theatres. In the devices disclosed by these two documents, scents, which are associated with the specific visual or acoustical event, are defused to viewers or listeners. U.S. Pat. No. 5,398,070 teaches the capture of images with scene scents and subsequent image display and scent emission device. The association of scents other media, such as photographic (U.S. Pat. No. 5,995,770) media and electrophotographic (U.S. Pat. No. 5,970,300) media, is a more recent development. U.S. Pat. No. 5,995,770 teaches the photographers'selection of scent for application to photographic images using a variety of delivery subsystems such as micro-encapsulation (scratch and sniff), poly-traps, microsponges as well as direct spraying of aerosol scents onto the back of a photographic print. However, this method does not enable application of scent delivery subsystems directly onto the photographic image. U.S. Pat. No. 5,970,300 teaches the method of application of liquid scents to a typical electrophotographic process. However, this method does not provide for application of scent delivery subsystems nor tactile delivery subsystems. Neither U.S. Pat. No. 5,995,770 nor U.S. Pat. No. 5,970,300 provide for an environmental protection barrier.

PROBLEM TO BE SOLVED BY THE INVENTION

There is a need for pressure sensitive labels for application to packages that are high in quality and at the same time economical for short runs. There is a further need for extending the appeal of a label to include olfactory and tactile senses.

SUMMARY OF THE INVENTION

It is an object of the invention to provide higher quality images to packaging materials.

It is a further object to provide packaging labels that are scented.

It is another object to provide printed labels that have tactile feel and texture.

These and other objects of the invention are accomplished by an image element comprising an image having at least one overcoat layer over said image comprising at least one tactile or olfactory feature.

ADVANTAGEOUS EFFECT OF THE INVENTION

The invention provides improved image quality for packaging materials. The invention also provides scented packaging materials and packaging materials that contain texture which allows products to be marketed to consumers using visual, tactile and olfactory messages. An image element comprising an image having at least one overcoat layer over said image comprising at least one tactile or olfactory feature.

DETAILED DESCRIPTION OF THE INVENTION

The invention has numerous advantages over prior practices in the art. Recently there has been a trend in the marketing of mass consumer items to try to localize the marketing to separately approach smaller groups. These groups may be regional, ethnic, gender, age, or special interest differentiated. In order to approach these different groups, there is a need to provide packaging that is specifically directed to these groups. As discussed above, the traditional packaging materials are generally suited for very long runs of material and to form shorter runs or to provide rapid changes in packaging is impossible or very expensive. We have found silver halide based photographic materials that are suitable for packaging uses. Further, recently there has become available rapid photo processing apparatus suitable for short runs of material. There is also available silver halide processing apparatus that is capable of high speed, relatively long continuous runs of material. The combination of low cost packaging suitable photographic material with the processing apparatus available for rapid short and long runs of material has resulted in the opportunity for silver halide material to be utilized in packaging materials. Silver halide materials that have properties such as flexibility, low cost, and the ability to flex and bend has resulted in materials satisfactory and suitable for packaging.

By combining the advantages of silver halide printing, mainly excellent image quality, short run economics and ability to print from a digital file with scent, high quality labels that appeal to consumers both visually and olfactory significantly improve the ability of advertiser to connect with the consumer. Further, by combining visual content with a scent that is consistent with a visual message, great synergy can be achieved between the image and the scent. For example, a silver halide label consisting of a hot cup of coffee contains scent materials that provide the label with a coffee smell or a cabernet sauvignon wine label that is scented with red berry common to the cabernet sauvignon grape. The desired scent can be delivered on the entire image or can be constrained to a specific geographical area on the image creating a "scent window".

A sensual label appeals to at least two human senses, for example a visual label can be further enhanced by the addition of texture to the surface of the label. By combining the excellent image quality of silver halide images, scent and texture, the label material of the invention has broad sensual appeal, appealing to three of the five human senses. The sensual label provides advertisers an opportunity to make a better connection with consumers by using multiple senses to experience the product on the shelf.

The utilization of the thin, flexible, and tough silver halide materials results in a packaging material having many superior properties. These materials are capable of having brighter, sharper, and higher color images than anything presently available in packaging. The packaging materials of the invention have a silver halide depth of image unsurpassed by existing packaging materials. The packaging materials of the invention may be further provided with a variety of packing materials that are suitable pressure sensitive labeling of packages such as shampoo bottles, perfume bottles and film boxes. The packaging materials of the invention while having the advantage of superior image are available on thin base materials which are low in cost while providing superior opacity and strength. The packaging materials of the invention as they may be imaged by flash optical exposure or digital printing have the ability to be formed in short runs and to be rapidly switched from one image to the next without delay.

The silver halide label materials of the invention allows packages to be rapidly designed and brought to market. For instance, significant events in sports or entertainment may be practically instantly brought to market as a digital image may be immediately flash exposed onto silver halide pressure sensitive labels and utilized within moments from the time of the event. This is in contrast to typical photogravure or flexographic imaging where lead times for pressure sensitive labels are typically several weeks. Further, the quality of the silver halide formed image lends itself to collectable images formed as a part of packaging much better than previous images which were of lower quality and were less desirable for collecting. Finally, the regional customization of images is rapidly possible.

The ability to rapidly change packaging also would find use in the need to provide regional labeling with different languages and marketing themes in different countries. Further, different countries have different legal labeling requirements as to content. For instance, alcoholic beverages such as wine and beer are subject to a wide variety of regional and national variations in labeling requirements. Wines manufactured in France may have long delays in shipping out of France due to the wait for national labeling in other countries. Photographic images also would be particularly desirable for premium products such as fine wines, perfumes, and chocolates, as they would be of high quality and reflect the high quality of the product in the package.

Just as product brands are easily identified by a brand color such as the Kodak Red and Yellow or the Kraft food yellow, brand identification may also be extended to a brand scent and a brand texture that are conveyed to the consumer by sensual labels. These and other advantages will be apparent from the detailed description below.

The terms as used herein, "top", "upper", "emulsion side", and "face" mean the side or toward the side of a photographic packaging label bearing the imaging layers. The term environmental protection layer means the layer applied to the imaging layers. The terms "face stock" and "substrate" mean the material to which the silver halide layers are applied. The terms "bottom", "lower side", "liner" and "back" mean the side or toward the side of the label or packaging material opposite from the side bearing the imaging layers or developed image.

Product advertising, in particularly, product labeling, is important in differentiating product on the shelf and conveying a message to the consumer. Prior art labels typically have used visual labels that consist of ink printed text, graphics and images. In order to better differentiate product and better communicate with the consumer, an image element comprising an image, at least one over coat layer and at least one tactile olfactory feature is preferred. By providing a tactile feature or an olfactory feature, the sensual label of the invention can be interpreted by more than one human sense and therefore be more effective than a typical visual label. A combination of a tactile feature and a olfactory feature further enables the ability to communicate with the consumer. An example of a preferred sensual label is a silver halide image of a pine tree, that smells of a fresh cut pine and has a surface texture that is similar to pine needles. If this sensual pine tree label were attached to a bottle containing a pine scented cleaning product, then the label communicated to the consumer using a visual, tactile and olfactory feature.

A preferred embodiment for delivery of the scent feature comprises a pressure releasable scent. A pressure releasable scent allows for the scent to be released by contact with retail store personnel or by the consumer when the product is handled. Pressure releasable scent is preferably complimentary to areas of the image. By correlation of visual data with scent data, the image and the scent are providing a message that is synergistic. For example, an image of a rose would smell of a rose and the balance of the image would be scent neutral. A preferred embodiment of the delivery of the tactile feature is a pressure release of a liquid. A pressure releasable liquid allows for a tactile liquid that may contain scent to be released from the image altering the tactile feel of the image and thus the sensual label. A preferred pressure sensitive releasable liquid is an oil based liquid. Oil based liquids are preferred as they can dramatically alter the tactile feel of an image with a small amount of material, typically less than 20 $mg/m^2$. The oil based liquids are also very efficient carriers of scent. A preferred embodiment for the release of scent is from particles of encapsulated scented oils. Encapsulated oils are preferred in that they can easily be coated in the imaging layer, the encapsulating particles hold the scent or oil based materials until time of release and can be released by pressure.

A preferred embodiment for providing the tactile feature to the imaging element is a layer coated on top of the image layers that contains texture. A textured overcoat layer is preferred as the overcoat layer protects the delicate imaging layers and because it is the outermost layer, the overcoat layer provides the most efficient means of providing a texture (texture provided in the imaging layers would be reduces as the overcoat layer reduces the texture by reducing surface roughness). In another preferred embodiment, the surface texture is provided on a portion of the image. This allows the visual content to be correlated to the texture content. An example would be an image of a beach containing sand. The portion of the image containing sand is preferably made rough and the balance of the image would remain smooth.

A preferred embodiment for a textured overcoat layer is incorporation of particles into the overcoat layer. By providing particles into the over coal layer, the surface texture of the image can be perceptually altered to provide differentiated tactile feel. The preferred average particle size for particle addition to the overcoat layer is between 2 and 500 micrometers. Particle sizes less than 1 micrometer have been shown to be too small to provide the desired tactile feel. Further, overcoat layers are typically thicker than 1 micrometer and therefore the particles would be entirely encapsulated within the overcoat layer. Particle sizes greater than 600 micrometers have been shown to be too large to be adhered to an overcoat layer. The most preferred average particle size is between 2 and 100 micrometers. Particle sizes between 2 and 100 micrometers have been shown to provide perceptual tactile feel.

Suitable particles include colloidal silica, colloidal alumina, and metal oxides such as tin oxide and aluminum oxide. The preferred particles are colloidal silica and alumina, most preferably, silica. The cross-linked polymer having a coating of an agent may be prepared by procedures well known in the art. For example, conventional suspension polymerization processes wherein the agent is added to the suspension is preferred. As the agent, colloidal silica is preferred. The particles can also be inorganic spheres, including solid or hollow glass spheres, metal or ceramic beads or inorganic particles such as clay, talc, barium sulfate, calcium carbonate.

Another preferred embodiment for a textured surface is a depth difference between the textured feature and the surrounding image. A depth difference has been shown to provide a tactile feel in that depth reduces the amount of contact area between the consumer and the image surface. The preferred depth difference is between 5 and 100 micrometers. A depth of less than 3 micrometers does not provide enough difference between the depth feature and the image. A depth of greater than 120 micrometers is not cost justified because the tactile feel does not significant improve. A preferred textured surface indicia comprises braille. Braille indicia provides a means for the visually impaired consumers to both purchase product and to identify the product when in use. The braille indicia is imparted to the surface by braille methods well known in the art. Typical method is embossing a braille message into the image layer or using lasers to create indentations.

A preferred method for increasing the surface roughness of smooth imaging layers is embossing roughness into the imaging layers by use of a commercially available embossing equipment. Imaging layers applied to web materials are transported through a nip that contains a nip roll and a impression roll. The impression roll under pressure and heat embosses the roll pattern onto the imaging layers. The surface roughness and pattern obtained during embossing is the result of the surface roughness and pattern on the embossing roll.

A preferred textured surface is a pattern. A patterned texture is preferred as it allows for a non-slip surface to be created for soap bottles that are utilized in the shower for example. The patterned surface a also allows for a combination of diffuse and specular light reflection which adds to the appeal of the imaged layers. A surface texture in intermittent areas is preferred in that the texture can be correlated to the scent feature or the image feature that is of interest.

In another preferred embodiment of the invention, the image element is provided with a olfactory feature and a olfactory barrier layer that partially overlays the image element containing the olfactory layer by means of coating over a mask. By providing a olfactory feature in the image layer and overlaying a olfactory barrier, a scent pattern can be created localizing the scent to areas of interest. For example, if an image of a pine tree in a forest contained pine scent, an olfactory barrier can be applied to the image such as on acrylic coated polymer coated with a mask in such a way as to cover all items in the image that is not related to the pine tree. The net result would be the pine tree smelling of pine and the balance of the image scent neutral.

In a preferred embodiment of the invention, the overlaying layer comprises gelatin. Gelatin has been found to be an excellent medium to deliver the scent feature and gelatin is commonly utilized for photosensitive imaging layers and ink jet dye receiving layers and therefore the overlaying layer comprising gelatin adheres well to gelatin based imaging layers.

The addition of a fiducial mark to the formed image is preferred as the fiducial mark provides a means for die cutting the image to create a label. The addition of a fiducial mark allows the imaging article to be die cut using optical sensors to read the registration of the image. The fiducial mark bay be printed on the base material, printed using silver halide formed images, ink jet receiving layers, thermal dye transfer receiving layers or post process printed using printed inks. In another embodiment, the fiducial mark is created utilizing a mechanical means such as punched hole, mechanical embossing or a partial punched hole to create a topographical difference in the silver halide formed image. A mechanical fiducial mark allows for mechanical sensors to be used for die cutting, application of a spot printed color or for locating a label on a package during a automated labeling.

In another embodiment of the invention, the silver halide formed image is preferably over laminated with a pre-printed sheet. By pre-printing a over lamination sheet with images, text or non-neutral color, the color space of the silver halide formed image is expanded. Further, over laminating also protects the delicate silver halide formed image from abrasion, water and handling damage that frequently occurs for packaging labels.

In a further embodiment of the invention, the photo image is preferably colored with magnetic recording materials. By coloring the image with magnetic recording materials, the photographic article can contain both visual information and magnetic information. Magnetic information can be utilized for product identification, storage of product information that is machine readable by retailers or consumers or as a means of providing a security feature. A magnetic recording layer can be used to record photographic processing information such as date and time of processing, voice or data from the capture device, or can be used to store a digital file of the printed image. More specifically, the colored magnetic recording layer increases the optical density of the backside biaxially oriented sheet by less than 0.2 optical density units across the visible portion of the spectrum from 400 nm to 700 nm.

In forming the transparent magnetic recording layer, magnetic particles with a surface area of 30 m.sup.2/gram are applied in a coated layer having a dried thickness less than 1.5 $\mu$m. The magnetic particles are homogeneously dispersed in a transparent binder and a solvent for the binder. An example of a magnetic binder is cellulose organic acid esters. Suitable solvents include methylene chloride, methyl alcohol, methyl ethyl ketone, methyl isobutyl ketone, ethyl acetate, butyl acetate, cyclohexanone, butyl alcohol, and mixtures thereof. The dispersing medium can also contain transparent addenda such as plasticizers and dispersing agents.

In order to produce a pressure sensitive photographic sensual label, the liner material that carries the pressure sensitive adhesive, face stock and silver halide imaged layers, the liner material must allow for efficient transport in manufacturing, image printing, image development, label converting and label application equipment. A label comprising a silver halide imaging layer, a base and a strippable liner adhesively connected by an adhesive to said base, wherein said base has a stiffness of between 15 and 60 millinewtons and an L* is greater than 92.0, and wherein said liner has a stiffness of between 40 and 120 millinewtons is preferred. The photographic label with expanded color gamut of the invention is preferred as the white, stiff liner allows for efficient transport through photographic printing and processing equipment and improves printing speed compared to typical liner materials that are brown or clear and have little contribution to secondary exposure.

A peelable liner or back is preferred as the pressure sensitive adhesive required for adhesion of the label to the package, can not be transported through labeling equipment without the liner. The liner provides strength for conveyance and protects the pressure sensitive adhesive prior to application to the package. A preferred liner material is cellulose paper. A cellulose paper liner is flexible, strong and low in cost compared to polymer substrates. Further, a cellulose paper substrate allows for a textured label surface that can be desirable in some packaging applications. The paper may be provided with coatings that will provide waterproofing to the paper as the photographic element of the invention must be processed in aqueous chemistry to develop the image. Examples of a suitable water proof coatings applied to the paper are acrylic polymer, melt extruded polyethylene and oriented polyolefin sheets laminated to the paper. Paper is also preferred as paper can contain moisture and salt which provide antistatic properties that prevent static sensitization of the silver halide image layers.

Further, paper containing sizing agents, known in the photographic paper art and disclosed in U.S. Pat. No. 6,093,521, provides resistance to edge penetration of the silver halide image processing chemistry. An edge penetration of less than 8 micrometers is preferred as processing chemistry penetrated into the paper greater than 12 micrometers has been shown to swell causing die cutting problems when face stock matrix is die cut and stripped from the liner. Also, penetration of processing chemistry greater than 12 micrometers increases the chemistry usage in processing resulting in a higher processing costs.

Another preferred liner material or peelable back is an oriented sheet of polymer. The liner preferably is an oriented polymer because of the strength and toughness developed in the orientation process. Preferred polymers for the liner substrate include polyolefins, polyester and nylon. Preferred polyolefin polymers include polypropylene, polyethylene, polymethylpentene, polystyrene, polybutylene, and mixtures thereof Polyolefin copolymers, including copolymers of propylene and ethylene such as hexene, butene, and octene are also useful. Polyester is most preferred, as it is has desirable strength and toughness properties required for efficient transport of silver halide pressure sensitive label liner in high speed labeling equipment.

In another preferred embodiment, the liner consists of a paper core to which sheets of oriented polymer are laminated. The laminated paper liner is preferred because the oriented sheets of polymer provide tensile strength which allows the thickness of the liner to be reduced compared to coated paper and the oriented polymer sheet provides resistance to curl during manufacturing and drying in the silver halide process.

The tensile strength of the liner or the tensile stress at which a substrate breaks apart is an important conveyance and forming parameter. Tensile strength is measured by ASTM D882 procedure. A tensile strength greater than 120 MPa is preferred as liners less than 110 MPa begin to fracture in automated packaging equipment during conveyance, forming and application to the package.

The coefficient of friction or COF of the liner bearing the silver halide imaging layer is an important characteristic as the COF is related to conveyance and forming efficiency in automated labeling equipment. COF is the ratio of the weight of an item moving on a surface to the force that maintains contact between the surface and the item. The mathematical expression for COF is as follows:

$$COF=\mu=(\text{friction force/normal force})$$

The COF of the liner is measured using ASTM D-1894 utilizing a stainless steel sled to measure both the static and dynamic COF of the liner. The preferred COF for the liner of the invention is between 0.2 and 0.6. As an example, a 0.2 COF is necessary for coating on a label used in a pick-and-place application. The operation using a mechanical device to pick a label and move it to another point requires a low COF so the label will easily slide over the surface of the label below it. At the other extreme, large sheets such as book covers require a 0.6 COF to prevent them from slipping and sliding when they are piled on top of each other in storage. Occasionally, a particular material may require a high COF on one side and a low COF on the other side. Normally, the base material itself, such as a plastic film, foil, or paper substrate, would provide the necessary COF for one side. Application of an appropriate coating would modify the image side to give the higher or lower value. Conceivably, two different coatings could be used with one on either side. COF can be static or kinetic. The coefficient of static friction is the value at the time movement between the two surfaces is ready to start but no actual movement has occurred. The coefficient of kinetic friction refers to the case when the two surfaces are actually sliding against each other at a constant rate of speed. COF is usually measured by using a sled placed on the surface. The force necessary at the onset of sliding provides a measurement of static COF. Pulling the sled at a constant speed over a given length provides a measure of kinetic frictional force.

The preferred thickness of the liner of the invention is between 75 and 225 micrometers. Thickness of the liner is important in that the strength of the liner, expressed in terms of tensile strength or mechanical modulus, must be balanced with the thickness of the liner to achieve a cost efficient design. For example, thick liners that are high in strength are not cost efficient because thick liners will result in short roll lengths compared to thin liners at a given roll diameter. A liner thickness less that 60 micrometer has been shown to cause transport failure in the edge guided silver halide printers. A liner thickness greater than 250 micrometers yields a design that is not cost effective and is difficult to transport in existing silver halide printers.

The liner of the invention preferably has an optical transmission of less than 20%. During the printing of the silver halide labels, exposure light energy is required to reflect from the face stock/liner combination to yield a secondary exposure. This secondary exposure is critical to maintaining high level of printing productivity. It has been shown that liners with an optical transmission of greater than 25% significantly reduces the printing speed of the silver halide label. Further, clear face stock material to provide the "no label look" need an opaque liner to not only maintain printing speed, but to prevent unwanted reflection from printing platens in current silver halide printers.

Since the light sensitive silver halide layers with expanded color gamut of the can suffer from unwanted exposure from static discharge during manufacturing, printing and processing, the liner preferably has a resistivity of less than $10^{11}$ ohms/square. A wide variety of electrically-conductive materials can be incorporated into antistatic layers to produce a wide range of conductivities. These can be divided into two broad groups: (i) ionic conductors and (ii) electronic conductors. In ionic conductors charge is transferred by the bulk diffusion of charged species through an electrolyte. Here the resistivity of the antistatic layer is dependent on temperature and humidity. Antistatic layers containing simple inorganic salts, alkali metal salts of surfactants, ionic conductive polymers, polymeric electrolytes containing alkali metal salts, and colloidal metal oxide sols (stabilized by metal salts), described previously in patent literature, fall in this category. However, many of the inorganic salts, polymeric electrolytes, and low molecular weight surfactants used are water-soluble and are leached out of the antistatic layers during processing, resulting in a loss of antistatic function. The conductivity of antistatic layers employing an electronic conductor depends on electronic mobility rather than ionic mobility and is independent of humidity. Antistatic layers which contain conjugated polymers, semiconductive metal halide salts, semiconductive metal oxide particles, etc. have been described previously. However, these antistatic layers typically contain a high volume percentage of electronically conducting materials which are often expensive and impart unfavorable physical characteristics, such as color, increased brittleness, and poor adhesion to the antistatic layer.

In a preferred embodiment of this invention the sensual label has an antistat material incorporated into the liner or coated on the liner. It is desirable to have an antistat that has an electrical surface resistivity of at least $10^{11}$ log ohms/square. In the most preferred embodiment, the antistat material comprises at least one material selected from the group consisting of tin oxide and vanadium pentoxide.

In another preferred embodiment of the invention antistatic material is incorporated into the pressure sensitive adhesive layers. The antistatic material incorporated into the pressure sensitive adhesive layer provides static protection to the silver halide layers and reduces the static on the sensual label which has been shown to aid labeling of containers in high speed labeling equipment. As a stand-alone or supplement to the liner comprising an antistatic layer, the pressure sensitive adhesive may also further comprise an antistatic agent selected from the group consisting of conductive metal oxides, carbon particles, and synthetic smectite clay, or multi-layered with an inherently conductive polymer. In one of the preferred embodiments, the antistat material is metal oxides. Metal oxides are preferred because they are readily dispersed in the thermoplastic adhesive and can be applied to the polymer sheet by any means known in the art. Conductive metal oxides that may be useful in this invention are selected from the group consisting of conductive particles including doped-metal oxides, metal oxides containing oxygen deficiencies, metal antimonates, conductive nitrides, carbides, or borides, for example, $TiO_2$, $SnO_2$, $Al._2O_3$, $ZrO_3$, $In_2O_3$, MgO, $ZnSb_2O_6$, $InSbO_4$, $TiB_2$, $ZrB_2$, $NbB_2$, $TaB_2$, $CrB_2$, MoB, WB, $LaB_6$, ZrN, TiN, TiC, and WC. The most preferred materials are tin oxide and vanadium pentoxide because they provide excellent conductivity and are transparent.

In order to provide a digital printing technology that can be applied to a package that is high in quality, can handle text, graphic and images, is economical for short run printing jobs and accurately reproduce flesh tones, silver halide imaging is preferred. The silver halide technology can be either black and white or color. The silver halide imaging layers are preferably exposed and developed prior to application to a package. The flexible substrate of the invention contains the necessary tensile strength properties and coefficient of friction properties to allow for efficient transport and application of the images in high speed labeling equipment. The substrate of the invention is formed by applying light sensitive silver halide imaging layers of a flexible sensual label stock that contains a pressure sensitive adhesive. The imaging layers, face stock and pressure sensitive adhesive are supported and transported through labeling equipment using a tough liner material. Because the light sensitive silver halide imaging layers are vulnerable to environmental solvents such as water, coffee and hand oils, an environmental protection layer is preferably applied to the light sensitive silver halide imaging layers after image development.

The environmental protection layer may consist of suitable material that protects the image from environmental solvents, resists scratching and does not interfere with the image quality. The environmental protection layer is preferably applied to the photographic image after image development because the liquid processing chemistry required for image development must be able to efficiently penetrate the surface of the imaging layers to contact the silver halide and couplers utilizing typical silver halide imaging processes. The environmental protection layer would be generally impervious to developer chemistry. An environmental protection layer where transparent polymer particles are applied to the top most surface of the imaging layers in the presence of an electric field and fused to the top most layer causing the transparent polymer particles to form a continuous polymeric layer is preferred. An electrophotographic toner applied polymer is preferred as it is an effective way to provide a thin, protective environmental layer to the photographic sensual label that has been shown to withstand environmental solvents and damage due to handling.

In another embodiment, the environmental protection layer is coatable from aqueous solution, which survives exposure and processing, and forms a continuous, water-impermeable protective layer in a post-process fusing step. The environmental protection layer is preferably formed by coating polymer beads or particles of 0.1 to 50 $\mu$m in average size together with a polymer latex binder on the emulsion side of a sensitized photographic product. Optionally, a small amount of water-soluble coating aids (viscosifiers, surfactants) can be included in the layer, as long as they leach out of the coating during processing. After exposure and processing, the product with image is treated in such a way as to cause fusing and coalescence of the coated polymer beads, by heat and/or pressure (fusing), solvent treatment, or other means so as to form the desired continuous, water impermeable protective layer.

Examples of suitable polymers from which the polymer particles used in environmental protection layer can be selected include poly(vinyl chloride), poly(vinylidene chloride), poly(vinyl chloride-co-vinylidene chloride), chlorinated polypropylene, poly(vinyl chloride-co-vinyl acetate), poly(vinyl chloride-co-vinyl acetate-co-maleic anhydride), ethyl cellulose, nitrocellulose, poly(acrylic acid) esters, linseed oil-modified alkyd resins, rosin-modified alkyd resins, phenol-modified alkyd resins, phenolic resins, polyesters, poly(vinyl butyral), polyisocyanate resins, polyurethanes, poly(vinyl acetate), polyamides, chroman resins, dammar gum, ketone resins, maleic acid resins, vinyl polymers, such as polystyrene and polyvinyltoluene or copolymer of vinyl polymers with methacrylates or acrylates, poly(tetrafluoroethylene-hexafluoropropylene), low-molecular weight polyethylene, phenol-modified pentaerythritol esters, poly(styrene-co-indene-co-acrylonitrile), poly(styrene-co-indene), poly(styrene-co-acrylonitrile), poly(styrene-co-butadiene), poly(stearyl methacrylate) blended with poly(methyl methacrylate), copolymers with siloxanes and polyalkenes. These polymers can be used either alone or in combination.

To increase the abrasion resistance of the environmental protection layer, polymers which are cross-linked or branched can be used. For example, poly(styrene-co-indene-co-divinylbenzene), poly(styrene-co-acrylonitrile-co-divinylbenzene), or poly(styrene-co-butadiene-co-divinylbenzene) can be used.

The polymer particles fused to form the environmental protection layer should be transparent, and are preferably colorless. But it is specifically contemplated that the polymer particle can have some color for the purposes of color correction, or for special effects, so long as the image is viewable through the overcoat. Thus, there can be incorporated into the polymer particle dye which will impart color. In addition, additives can be incorporated into the polymer particle which will give to the overcoat desired properties. For example, a UV absorber can be incorporated into the polymer particle to make the overcoat UV absorptive, thus protecting the image from UV induced fading or blue tint can be incorporated into the polymer particle to offset the native yellowness of the gelatin used in the silver halide imaging, layers.

In addition to the fusible polymer particles which form the environmental protection layer there can be combined with the polymer composition other particles which will modify the surface characteristics of the element. Such particle are solid and nonfusible at the conditions under which the polymer particles are fused, and include inorganic particles, like silica, and organic particles, like methylmethacrylate beads, which will not melt during the fusing step and which will impart surface roughness to the overcoat.

The surface characteristics of the environmental protection layer are in large part dependent upon the physical characteristics of the polymer which forms the toner and the presence or absence of solid, nonfusible particles. However, the surface characteristics of the overcoat also can be modified by the conditions under which the surface is fused. For example, the surface characteristics of the fusing member that is used to fuse the toner to form the continuous overcoat layer can be selected to impart a desired degree of smoothness, texture or pattern to the surface of the element. Thus, a highly smooth fusing member will give a glossy surface to the imaged element, a textured fusing member will give a matte or otherwise textured surface to the element, a patterned fusing member will apply a pattern to the surface of the element.

Suitable examples of the polymer latex binder include a latex copolymer of butyl acrylate, 2-acrylamido-2-methylpropanesulfonate, and acetoacetoxyethylmethacrylate. Other latex polymers which are useful include polymers having a 20 to 10,000 nm diameter and a Tg of less than 60° C. suspended in water as a colloidal suspension.

Examples of suitable coating aids for the environmental protection layer include any water soluble polymer or other material that imparts appreciable viscosity to the coating suspension, such as high MW polysaccharide derivatives (e.g. xanthan gum, guar gum, gum acacia, Keltrol (an anionic polysaccharide supplied by Merck and Co., Inc.) high MW polyvinyl alcohol, carboxymethylcellulose, hydroxyethylcellulose, polyacrylic acid and its salts, polyacrylamide, etc). Surfactants include any surface active material that will lower the surface tension of the coating preparation sufficiently to prevent edge-withdrawal, repellencies, and other coating defects. These include alkyloxy- or alkylphenoxypolyether or polyglycidol derivatives and their sulfates, such as nonylphenoxypoly(glycidol) available from Olin Matheson Corporation or sodium octylphenoxypoly(ethyleneoxide) sulfate, organic sulfates or sulfonates, such as sodium dodecyl sulfate, sodium dodecyl sulfonate, sodium bis(2-ethylhexyl)sulfosuccinate (Aerosol OT), and alkylcarboxylate salts such as sodium decanoate.

The application of a ultraviolet polymerizable monomers and oligomers to the outermost layer of the developed silver halide imaging layers and subsequent radiation exposure to form a thin cross-linked protective layer is preferred. UV cure polymers are preferred as they can easily be applied to the outermost layer of the silver halide imaging layers and have been shown to provide an acceptable protective layer for the silver halide sensual label material. Preferred UV cure polymers include aliphatic urethane, allyl methacrylate, ethylene glycol dimethacrylate, polyisocyanate and hydroxyethyl methacrylate. A preferred photoinitiator is benzil dimethyl ketal. The preferred intensity of radiation is between 0.1 and 1.5 milliwatt/$cm^2$. Below 0.05, insufficient cross linking occurs yielding a protective layer that does not offer sufficient protection for the labeling of packages.

The application of a pre-formed polymer layer to the outermost surface of the developed sensual label silver halide image to form an environmental protection layer is most preferred. Application of a pre-formed sheet is preferred because pre-formed sheets are tough and durable easily withstanding the environmental solvents and handling forces applied to the silver halide imaged sensual label. Application of the pre-formed polymer sheet is preferable carried out though lamination after image development. An adhesive is applied to either the photographic sensual label or the pre-formed polymer sheet prior to a pressure nip that adheres the two surfaces and eliminates any trapped air that would degrade the quality of the image.

The pre-formed sheet preferably is an oriented polymer because of the strength and toughness developed in the orientation process. Preferred polymers for the flexible substrate include polyolefins, polyester and nylon. Preferred polyolefins include polypropylene, polyethylene, polymethylpentene, polystyrene, polybutylene, and mixtures thereof. Polyolefin copolymers, including copolymers of propylene and ethylene such as hexene, butene, and octene are also useful. Polypropylene is most preferred, as it is low in cost and has desirable strength and toughness properties required for a pressure sensitive sensual label.

The application of a synthetic latex to the developed silver halide sensual label image is another preferred environmental protection layer. A coating of synthetic latex has been shown to provide an acceptable environmental protection layer and can be coated in an aqueous solution eliminating exposure to solvents. The coating of latex has been shown to provide an acceptable environmental protection layer for the silver halide packaging sensual label. Preferred synthetic latexes for the environmental protection layer are made by emulsion polymerization techniques from styrene butadiene copolymer, acrylate resins, and polyvinyl acetate. Polyurethane and polyvinyl latex materials may also be utilized. The preferred particle size for the synthetic latex ranges from 0.05 to 0.15 $\mu$m. The synthetic latex is applied to the outermost layer of the silver halide imaging layers by known coating methods that include rod coating, roll coating and hopper coating. The synthetic latexes must be dried after application and must dry transparent so as not to interfere with the quality of the silver halide image.

The base material, or the flexible substrate utilized in this invention on to which the light sensitive silver halide imaging layers are applied, must not interfere with the silver halide imaging layers. Further, the base material of this invention needs to optimize the performance of the silver halide imaging system. Suitable flexible substrates must also perform efficiently in a automated packaging equipment for the application of sensual labels to various containers. A preferred flexible substrate is cellulose paper. A cellulose paper substrate is flexible, strong and low in cost compared to polymer substrates. Further, a cellulose paper substrate allows for a textured sensual label surface that can be desirable in some packaging applications. The paper may be provided with coatings that will provide waterproofing to the paper as the photographic element of the invention must be processed in aqueous chemistry to develop the silver halide image. An example of a suitable coating is acrylic or polyethylene polymer.

Polymer substrates are another preferred base material because they are tear resistant, have excellent conformability, good chemical resistance and are high in strength. Preferred polymer substrates include polyester, oriented polyolefin such as polyethylene and polypropylene, cast polyolefins such as polypropylene and polyethylene, polystyrene, acetate and vinyl. Polymers are preferred as they are strong and flexible and provide an excellent surface for the coating of silver halide imaging layers.

Biaxially oriented polyolefin sheets are preferred as they are low in cost, have excellent optical properties that optimize the silver halide system and can be applied to packages in high speed labeling equipment. Microvoided composite biaxially oriented sheets are most preferred because the voided layer provides opacity and lightness without the need for $TiO_2$. Also, the voided layers of the microvoided biaxially oriented sheets have been shown to significantly reduce pressure sensitivity of the silver halide imaging layers. Microvoided biaxially oriented sheets are conveniently manufactured by coextrusion of the core and surface layers, followed by biaxial orientation, whereby voids are formed around void-initiating material contained in the core layer. Such composite sheets are disclosed in U.S. Pat. Nos. 4,377,616; 4,758,462; 4,632,869 and 5,866,282. The biaxially oriented polyolefin sheets also may be laminated to one or both sides of a paper sheet to form a sensual label with greater stiffness if that is needed.

The flexible polymer base substrate may contain more than one layer. The skin layers of the flexible substrate can be made of the same polymeric materials as listed above for the core matrix. The composite sheet can be made with skin(s) of the same polymeric material as the core matrix, or it can be made with skin(s) of different polymeric composition than the core matrix. For compatibility, an auxiliary layer can be used to promote adhesion of the skin layer to the core.

Voided biaxially oriented polyolefin sheets are a preferred flexible base substrate for the coating of light sensitive silver halide imaging layers. Voided films are preferred as they provide opacity, whiteness and image sharpness to the image. "Void" is used herein to mean devoid of added solid and liquid matter, although it is likely the "voids" contain gas. The void-initiating particles which remain in the finished packaging sheet core should be from 0.1 to 10 $\mu$m in diameter and preferably round in shape to produce voids of the desired shape and size. The size of the void is also dependent on the degree of orientation in the machine and transverse directions. Ideally, the void would assume a shape which is defined by two opposed and edge contacting concave disks. In other words, the voids tend to have a lens-like or biconvex shape. The voids are oriented so that the two major dimensions are aligned with the machine and transverse directions of the sheet. The Z-direction axis is a minor dimension and is roughly the size of the cross diameter of the voiding particle. The voids generally tend to be closed cells, and thus there is virtually no path open from one side of the voided-core to the other side through which gas or liquid can traverse.

The photographic element of this invention generally has a glossy surface, that is, a surface that is sufficiently smooth to provide excellent reflection properties. An opalescent surface may be preferred because it provides a unique photographic appearance to a sensual label that is perceptually preferred by consumers. The opalescent surface is achieved when the microvoids in the vertical direction are between 1 and 3 μm. By the vertical direction, it is meant the direction that is perpendicular to the plane of the imaging member. The thickness of the microvoids preferably is between 0.7 and 1.5 μm for best physical performance and opalescent properties. The preferred number of microvoids in the vertical direction is between 8 and 30. Less than 6 microvoids in the vertical direction do not create the desired opalescent surface. Greater than 35 microvoids in the vertical direction do not significantly improve the optical appearance of the opalescent surface.

The void-initiating material for the flexible base substrate may be selected from a variety of materials and should be present in an amount of about 5 to 50% by weight based on the weight of the core matrix polymer. Preferably, the void-initiating material comprises a polymeric material. When a polymeric material is used, it may be a polymer that can be melt-mixed with the polymer from which the core matrix is made and be able to form dispersed spherical particles as the suspension is cooled down. Examples of this would include nylon dispersed in polypropylene, polybutylene terephthalate in polypropylene, or polypropylene dispersed in polyethylene terephthalate. If the polymer is preshaped and blended into the matrix polymer, the important characteristic is the size and shape of the particles. Spheres are preferred and they can be hollow or solid. These spheres may be made from cross-linked polymers which are members selected from the group consisting of an alkenyl aromatic compound having the general formula $Ar—C(R)═CH_2$, wherein Ar represents an aromatic hydrocarbon radical, or an aromatic halohydrocarbon radical of the benzene series and R is hydrogen or the methyl radical; acrylate-type monomers include monomers of the formula $CH_2═C(R')—C(O)(OR)$ wherein R is selected from the group consisting of hydrogen and an alkyl radical containing from about 1 to 12 carbon atoms and R' is selected from the group consisting of hydrogen and methyl; copolymers of vinyl chloride and vinylidene chloride, acrylonitrile and vinyl chloride, vinyl bromide, vinyl esters having formula $CH_2═CH(O)COR$, wherein R is an alkyl radical containing from 2 to 18 carbon atoms; acrylic acid, methacrylic acid, itaconic acid, citraconic acid, maleic acid, fumaric acid, oleic acid, vinylbenzoic acid; the synthetic polyester resins which are prepared by reacting terephthalic acid and dialkyl terephthalics or ester-forming derivatives thereof, with a glycol of the series $HO(CH_2)_nOH$ wherein n is a whole number within the range of 2–10 and having reactive olefinic linkages within the polymer molecule, the above-described polyesters which include copolymerized therein up to 20 percent by weight of a second acid or ester thereof having reactive olefinic unsaturation and mixtures thereof, and a cross-linking agent selected from the group consisting of divinylbenzene, diethylene glycol dimethacrylate, diallyl fumarate, diallyl phthalate, and mixtures thereof.

Examples of typical monomers for making the cross-linked polymer void initiating particles include styrene, butyl acrylate, acrylamide, acrylonitrile, methyl methacrylate, ethylene glycol dimethacrylate, vinyl pyridine, vinyl acetate, methyl acrylate, vinylbenzyl chloride, vinylidene chloride, acrylic acid, divinylbenzene, acrylamidomethyl-propane sulfonic acid, vinyl toluene, etc. Preferably, the cross-linked polymer is polystyrene or poly (methyl methacrylate). Most preferably, it is polystyrene, and the cross-linking agent is divinylbenzene.

Processes well known in the art yield nonuniformly sized void initiating particles, characterized by broad particle size distributions. The resulting beads can be classified by screening the beads spanning the range of the original distribution of sizes. Other processes such as suspension polymerization, limited coalescence, directly yield very uniformly sized particles.

The void-initiating materials may be coated with agents to facilitate voiding. Suitable agents or lubricants include colloidal silica, colloidal alumina, and metal oxides such as tin oxide and aluminum oxide. The preferred agents are colloidal silica and alumina, most preferably, silica. The cross-linked polymer having a coating of an agent may be prepared by procedures well known in the art. For example, conventional suspension polymerization processes wherein the agent is added to the suspension is preferred. As the agent, colloidal silica is preferred.

The void-initiating particles can also be inorganic spheres, including solid or hollow glass spheres, metal or ceramic beads or inorganic particles such as clay, talc, barium sulfate, or calcium carbonate. The important thing is that the material does not chemically react with the core matrix polymer to cause one or more of the following problems: (a) alteration of the crystallization kinetics of the matrix polymer, making it difficult to orient, (b) destruction of the core matrix polymer, (c) destruction of the void-initiating particles, (d) adhesion of the void-initiating particles to the matrix polymer, or (e) generation of undesirable reaction products, such as toxic or high color moieties. The void-initiating material should not be photographically active or degrade the performance of the photographic element in which the biaxially oriented polyolefin sheet is utilized.

The total thickness of the topmost skin layer of the polymeric base substrate may be between 0.20 μm and 1.5 μm, preferably between 0.5 and 1.0 μm. Below 0.5 μm any inherent nonplanarity in the coextruded skin layer may result in unacceptable color variation. At skin thickness greater than 1.0 μm, there is a reduction in the photographic optical properties such as image resolution. At thickness greater than 1.0 μm, there is also a greater material volume to filter for contamination such as clumps or poor color pigment dispersion.

Addenda may be added to the top most skin layer of the flexible base substrate to change the color of the imaging element. For labeling use, a white substrate with a slight bluish tinge is preferred. The addition of the slight bluish tinge may be accomplished by any process which is known in the art including the machine blending of color concentrate prior to extrusion and the melt extrusion of blue colorants that have been preblended at the desired blend ratio. Colored pigments that can resist extrusion temperatures greater than 320° C. are preferred, as temperatures greater than 320° C. are necessary for coextrusion of the skin layer. Blue colorants used in this invention may be any colorant that does not have an adverse impact on the imaging element. Preferred blue colorants include Phthalocyanine blue pigments, Cromophtal blue pigments, Irgazin blue pigments, and Irgalite organic blue pigments. Optical brightener may also be added to the skin layer to absorb UV energy and emit light largely in the blue region. $TiO_2$ may also be added to the skin layer. While the addition of $TiO_2$ in the thin skin layer of this invention does not significantly contribute to the optical performance of the sheet, it can cause numerous manufacturing problems such as extrusion die lines and spots. The skin layer substantially free of $TiO_2$ is preferred. $TiO_2$ added to a layer between 0.20 and 1.5 μm does not substantially improve the optical properties of the support, will add cost to the design, and will cause objectionable pigments lines in the extrusion process.

Addenda may be added to the core matrix and/or to one or more skin layers to improve the optical properties of the flexible substrate. Titanium dioxide is preferred and is used in this invention to improve image sharpness or MTF, opacity, and whiteness. The $TiO_2$ used may be either anatase or rutile type. Further, both anatase and rutile $TiO_2$ may be blended to improve both whiteness and sharpness. Examples of $TiO_2$ that are acceptable for a photographic system are DuPont Chemical Co. R101 rutile $TiO_2$ and DuPont Chemical Co. R104 rutile $TiO_2$. Other pigments known in the art to improve photographic optical responses may also be used in this invention. Examples of other pigments known in the art to improve whiteness are talc, kaolin, $CaCO_3$, $BaSO_4$, ZnO, $TiO_2$, ZnS, and $MgCO_3$. The preferred $TiO_2$ type is anatase, as anatase $TiO_2$ has been found to optimize image whiteness and sharpness with a voided layer.

The voids provide added opacity to the flexible substrate. This voided layer can also be used in conjunction with a layer that contains at least one pigment from the group consisting of $TiO_2$, $CaCO_3$, clay, $BaSO_4$, ZnS, $MgCO_3$, talc, kaolin, or other materials that provide a highly reflective white layer in said film of more than one layer. The combination of a pigmented layer with a voided layer provides advantages in the optical performance of the final image.

The flexible biaxially base substrate of this invention which has a microvoided core is preferred. The microvoided core adds opacity and whiteness to the imaging support, further improving imaging quality. Combining the image quality advantages of a microvoided core with a material, which absorbs ultraviolet energy and emits light in the visible spectrum, allows for the unique optimization of image quality, as the image support can have a tint when exposed to ultraviolet energy yet retain excellent whiteness when the image is viewed using lighting that does not contain significant amounts of ultraviolet energy such as indoor lighting.

It has been found that the microvoids located in the voided layer of the flexible biaxially oriented substrate provide a reduction in undesirable pressure fog. Mechanical pressure, of the order of hundreds of kilograms per square centimeter, causes an undesirable, reversible decrease in sensitivity by a mechanism at the time of writing that is not fully understood. The net result of mechanical pressure is an unwanted increase in density, mainly yellow density. The voided layer in the biaxially oriented flexible substrate absorbs mechanical pressure by compression of the voided layer, common in the converting and photographic processing steps, and reduces the amount of yellow density change. Pressure sensitivity is measured by applying a 206 MPa load to the coated light sensitive silver halide emulsion, developing the yellow layer, and measuring the density difference with an X-Rite model 310 (or comparable) photographic transmission densitometer between the control sample which was unloaded and the loaded sample. The preferred change in yellow layer density is less than 0.02 at a pressure of 206 MPa. A 0.04 change in yellow density is perceptually significant and, thus, undesirable.

The coextrusion, quenching, orienting, and heat setting of the flexible base substrate may be effected by any process which is known in the art for producing oriented sheet, such as by a flat sheet process or a bubble or tubular process. The flat sheet process involves extruding the blend through a slit die and rapidly quenching the extruded web upon a chilled casting drum so that the core matrix polymer component of the sheet and the skin components(s) are quenched below their glass solidification temperature. The quenched sheet is then biaxially oriented by stretching in mutually perpendicular directions at a temperature above the glass transition temperature and below the melting temperature of the matrix polymers. The sheet may be stretched in one direction and then in a second direction or may be simultaneously stretched in both directions. After the sheet has been stretched, it is heat set by heating to a temperature sufficient to crystallize or anneal the polymers, while restraining to some degree the sheet against retraction in both directions of stretching.

By having at least one nonvoided skin on the microvoided core, the tensile strength of the flexible base substrate is increased and makes the sheet more manufacturable. The higher tensile strength also allows the sheets to be made at wider widths and higher draw ratios than when sheets are made with all layers voided. Coextruding the layers further simplifies the manufacturing process.

A flexible sensual label base that is transparent may be preferred. A transparent flexible sensual label base is used to provide a clear pressure sensitive sensual label particularly useful for labeling applications that allow the contents of the package to be viewed though the label. Examples include wine bottle labeling, shampoo bottle labeling and beverage bottles that utilize clear or colored glass. For this invention, "transparent" material is defined as a material that has a spectral transmission greater than 90%. For a imaging element, spectral transmission is the ratio of the transmitted power to the incident power and is expressed as a percentage as follows; $T_{RGB}=10^{-D}*100$ where D is the average of the red, green and blue Status A transmission density response measured by an X-Rite model 310 (or comparable) photographic transmission densitometer.

A flexible sensual label base that has an optical transmission less than 20% is preferred for most applications. Optical transmission less than 20% provide a superior opaque silver halide pressure sensitive sensual label that is highly reflective. Opaque, highly reflective sensual labels are useful for pressure sensitive labeling against a background that is dark and would interfere with the quality of the image. An example would be the labeling of a black package, a sensual label base with optical transmission greater than 20% would darken the image, resulting is a loss of low density detail such as facial detail content.

A pressure sensitive photographic sensual label adhesive is utilized in the invention to allow the developed silver halide packaging sensual label to be adhered to the surface of the package typically utilizing high speed packaging equipment. "Peelable separation" or "peel strength" or "separation force" is a measure of the amount of force required to separate the silver halide sensual label from the package to which the sensual label has been applied. The peel strength is the amount of force required to separate two surfaces that are held together by internal forces of the photographic sensual label adhesive which consist of valence forces or interlocking action, or both. Peel strength is measured using an Instron gauge and peeling the sample at 180 degrees with a crosshead speed of 1.0 meters/min. The sample width is 5 cm and the distance peeled is 10 cm in length.

A peelable photographic sensual label adhesive is utilized to allow the consumer to separate the sensual label from the package. Separation of the label from the package would allow for example, rebate coupons to be attached to the package or used to for consumer promotions. For a peelable photographic label adhesive, the preferred peel strength between the silver halide pressure sensitive sensual label and the package is no greater than 80 grams/cm. A peel strength greater than 100 grams/cm, consumers would begin to have difficulty separating the image from the package. Further, at peel strengths greater than 110 grams/cm, the force is beginning to approach the internal strength of paper substrate, causing an unwanted fracture of the paper substrate before the separation of the image.

Upon separation of the image from the substrate, the peelable photographic sensual label adhesive of this invention has a preferred repositioning peel strength between 20 grams/cm and 100 grams/cm. Repositioning peel strength is the amount of force required to peel the separated image containing an photographic label adhesive from a stainless steel block at 23° C. and 50% RH. At repositioning peel strengths less than 15 grams/cm, the photographic label adhesive Lacks sufficient peel strength to remain adhered to a variety of surfaces such as refrigerators or photo albums. At peel strengths greater than 120 grams/cm, the photographic label adhesive of this invention is too aggressive, not allowing the consumer to later reposition the image.

The peelable photographic sensual label adhesive of this invention may be a single layer or two or more layers. For two or more photographic label adhesive layers, one of the photographic label adhesive layers preferentially adheres to the label base. As the image is separated from the substrate, this allows the photographic label adhesive of this invention be adhered to the label base for repositioning.

A substrate that comprises a release layer for a photographic sensual label adhesive that repositions is preferred. The release layer allows for uniform separation of the photographic label adhesive at the photographic label adhesive base interface. The release layer may be applied to the liner by any method known in the art for applying a release layer to substrates. Examples include silicone coatings, tetrafluoroethylene fluorocarbon coatings, fluorinated ethylene-propylene coatings, and calcium stearate.

Suitable peelable photographic sensual label adhesives utilized in this invention must not interact with the light sensitive silver halide imaging system so that image quality is deteriorated. Further, since photographic elements of this invention must be photoprocessed, the performance of the photographic label adhesive of this invention must not be deteriorated by photographic processing chemicals. Suitable photographic label adhesive may be inorganic or organic, natural or synthetic, that is capable of bonding the image to the desired surface by surface attachment. Examples of inorganic photographic sensual label adhesives are soluble silicates, ceramic and thermosetting powdered glass. Organic photographic sensual label adhesives may be natural or synthetic. Examples of natural organic photographic sensual label adhesives include bone glue, soybean starch cellulosics, rubber latex, gums, terpene, mucilages and hydrocarbon resins. Examples of synthetic organic photographic sensual label adhesives include elastomer solvents, polysulfide sealants, thermoplastic resins such as isobutylene and polyvinyl acetate, thermosetting resins such as epoxy, phenoformaldehyde, polyvinyl butyral and cyanoacrylates and silicone polymers. For single or multiple layer photographic sensual label adhesive systems, the preferred photographic label adhesive composition is selected from the group consisting of natural rubber, synthetic rubber, acrylics, acrylic copolymers, vinyl polymers, vinyl acetate-, urethane, acrylate-type materials, copolymer mixtures of vinyl chloride-vinyl acetate, polyvinylidene, vinyl acetate-acrylic acid copolymers, styrene butadiene, carboxylated stryrene butadiene copolymers, ethylene copolymers, polyvinyl alcohol, polyesters and copolymers, cellulosic and modified cellulosic, starch and modified starch compounds, epoxies, polyisocyanate, polyimides.

Water based pressure sensitive adhesion provide some advantages for the manufacturing process of non solvent emissions. Repositionable peelable photographic label adhesive containing non-photographic label adhesive solid particles randomly distributed in the photographic label adhesive layer aids in the ability to stick and then remove the print to get the desired end result. The most preferred pressure sensitive peelable photographic label adhesive is a respositionable photographic label adhesive layer containing at about 5% to 20% by weight of a permanent photographic label adhesive such as isooctyl acrylate/acrylic acid copolymer and at about 95% to 80% by weight of a tacky elastomeric material such as acrylate microspheres with the photographic label adhesive layer coverage at about 5 to 20 $g/m^2$.

The preferred peelable photographic sensual label adhesive materials may be applied using a variety of methods known in the art to produce thin, consistent photographic label adhesive coatings. Examples include gravure coating, rod coating, reverse roll coating, and hopper coating. The photographic label adhesives may be coated on the liner or the base materials prior to lamination.

For single or multiple layer photographic sensual label adhesive systems, the preferred permanent photographic sensual label adhesive composition is selected from the group consisting of epoxy, phenoformaldehyde, polyvinyl butyral, cyanoacrylates, rubber based photographic sensual label adhesives, styrene/butadiene based photographic label adhesives, acrylics and vinyl derivatives. Peelable photographic label adhesives and permanent photographic label adhesives may be used in combination in the same layer or in different locations in the photographic support structure. An example of a combination photographic label adhesive structure is a peelable photographic label adhesive between the top biaxially oriented sheet and the base materials and a permanent photographic label adhesive between the bottom biaxially oriented sheet and the base material.

The silver halide imaging layers on a pressure sensitive substrate preferably are applied to a variety of packages in automated labeling equipment. Preferred package types are bottles, can, stand up pouch, box and a bag. The packages may contain materials that require a package for sale. Preferred materials that are packaged include liquids and particulate materials.

The silver halide packaging sensual label of the invention preferably has a thickness of less than 600 $\mu$m. A silver halide packaging label greater than 650 $\mu$m offers no significant improvement in either imaging quality or packaging label performance. Further, transport through high speed packaging equipment is difficult at a photographic label thickness greater than 650 $\mu$m and stripping the photographic labels utilizing the Bernoulli method is difficult if the thickness of the photographic label exceeds 700 $\mu$m.

As used herein, the phrase "sensual label" is a element that is used to generate images by the techniques of ink jet printing, thermal dye transfer or electrophotographic printing, as well as a support for silver halide images. As used herein, the phrase "photographic element" is a material that utilizes photosensitive silver halide in the formation of images. The imaging elements above provide high quality images compared to ink printed images commonly utilized for labeling purposes. The thermal dye image-receiving layer of the receiving elements of the invention may comprise, for example, a polycarbonate, a polyurethane, a polyester, polyvinyl chloride, poly(styrene-co-acrylonitrile), poly(caprolactone), or mixtures thereof. The dye image-receiving layer may be present in any amount which is effective for the intended purpose. In general, good results have been obtained at a concentration of from about 1 to about 10 $g/m^2$. An overcoat layer may be further coated over the dye-receiving layer, such as described in U.S. Pat. No. 4,775,657 of Harrison et al.

Dye-donor elements that are used with the dye-receiving element of the invention conventionally comprise a support having thereon a dye containing layer. Any dye can be used in the dye-donor employed in the invention, provided it is transferable to the dye-receiving layer by the action of heat. Especially good results have been obtained with sublimable dyes. Dye donors applicable for use in the present invention are described, e.g., in U.S. Pat. Nos. 4,916,112; 4,927,803 and 5,023,228.

As noted above, dye-donor elements are used to form a dye transfer image. Such a process comprises image-wise-heating a dye-donor element and transferring a dye image to a dye-receiving element as described above to form the dye transfer image.

In a preferred embodiment of the thermal dye transfer method of printing, a dye donor element is employed which compromises a poly-(ethylene terephthalate) support coated with sequential repeating areas of cyan, magenta, and yellow dye, and the dye transfer steps are sequentially performed for each color to obtain a three-color dye transfer image. Of course, when the process is only performed for a single color, then a monochrome dye transfer image is obtained.

Thermal printing heads which can be used to transfer dye from dye-donor elements to receiving elements of the invention are available commercially. There can be employed, for example, a Fujitsu Thermal Head (FTP-040 MCS001), a TDK Thermal Head F415 HH7-1089, or a Rohm Thermal Head KE 2008-F3. Alternatively, other known sources of energy for thermal dye transfer may be used, such as lasers as described in, for example, GB No. 2,083,726A.

A thermal dye transfer assemblage of the invention comprises (a) a dye-donor element, and (b) a dye-receiving element as described above, the dye-receiving element being in a superposed relationship with the dye-donor element so that the dye layer of the donor element is in contact with the dye image-receiving layer of the receiving element.

When a three-color image is to be obtained, the above assemblage is formed on three occasions during the time when heat is applied by the thermal printing head. After the first dye is transferred, the elements are peeled apart. A second dye-donor element (or another area of the donor element with a different dye area) is then brought in register with the dye-receiving element and the process repeated. The third color is obtained in the same manner.

The electrographic and electrophotographic processes and their individual steps have been well described in detail in many books and publications. The processes incorporate the basic steps of creating an electrostatic image, developing that image with charged, colored particles (toner), optionally transferring the resulting developed image to a secondary substrate, and fixing the image to the substrate. There are numerous variations in these processes and basic steps; the use of liquid toners in place of dry toners is simply one of those variations.

The first basic step, creation of an electrostatic image, can be accomplished by a variety of methods. The electrophotographic process of copiers uses imagewise photodischarge, through analog or digital exposure, of a uniformly charged photoconductor. The photoconductor may be a single-use system, or it may be rechargeable and reimageable, like those based on selenium or organic photoreceptors.

In one form of the electrophotographic process, copiers use imagewise photodischarge through analog or digital exposure of a uniformly charged photoconductor. The photoconductor may be a single-use system, or it may be rechargeable and reimageable, like those based on selenium or organic photoreceptors.

In an alternate electrographic process, electrostatic images are created ionographically. The latent image is created on dielectric (charge-holding) medium, either paper or film. Voltage is applied to selected metal styli or writing nibs from an array of styli spaced across the width of the medium, causing a dielectric breakdown of the air between the selected styli and the medium. Ions are created, which form the latent image on the medium.

Electrostatic images, however generated, are developed with oppositely charged toner particles. For development with liquid toners, the liquid developer is brought into direct contact with the electrostatic image. Usually a flowing liquid is employed, to ensure that sufficient toner particles are available for development. The field created by the electrostatic image causes the charged particles, suspended in a nonconductive liquid, to move by electrophoresis. The charge of the latent electrostatic image is thus neutralized by the oppositely charged particles. The theory and physics of electrophoretic development with liquid toners are well described in many books and publications.

If a reimageable photoreceptor or an electrographic master is used, the toned image is transferred to paper (or other substrate). The paper is charged electrostatically with the polarity chosen to cause the toner particles to transfer to the paper. Finally, the toned image is fixed to the paper. For self-fixing toners, residual liquid is removed from the paper by air-drying or heating. Upon evaporation of the solvent, these toners form a film bonded to the paper. For heat-fusible toners, thermoplastic polymers are used as part of the particle. Heating both removes residual liquid and fixes the toner to paper.

The dye receiving layer or DRL for ink jet imaging may be applied by any known methods. Such as solvent coating, or melt extrusion coating techniques. The DRL is coated over the TL (tie layer) at a thickness ranging from 0.1–10 $\mu$m, preferably 0.5–5 $\mu$m. There are many known formulations which may be useful as dye receiving layers. The primary requirement is that the DRL is compatible with the inks which it will be imaged so as to yield the desirable color gamut and density. As the ink drops pass through the DRL, the dyes are retained or mordanted in the DRL, while the ink solvents pass freely through the DRL and are rapidly absorbed by the TL. Additionally, the DRL formulation is preferably coated from water, exhibits adequate adhesion to the TL, and allows for easy control of the surface gloss.

For example, Misuda et al in U.S. Pat. Nos. 4,879,166; 5,264,275; 5,104,730; 4,879,166, and Japanese Patents 1,095,091; 2,276,671; 2,276,670; 4,267,180; 5,024,335; and 5,016,517 discloses aqueous based DRL formulations comprising mixtures of psuedo-bohemite and certain water soluble resins. Light in U.S. Pat. Nos. 4,903,040; 4,930,041; 5,084,338; 5,126,194; 5,126,195; and 5,147,717 discloses aqueous-based DRL formulations comprising mixtures of vinyl pyrrolidone polymers and certain water-dispersible and/or water-soluble polyesters, along with other polymers and addenda. Butters et al in U.S. Pat. Nos. 4,857,386 and 5,102,717 disclose ink-absorbent resin layers comprising mixtures of vinyl pyrrolidone polymers and acrylic or methacrylic polymers. Sato et al in U.S. Pat. No. 5,194,317 and Higuma et al in U.S. Pat. No. 5,059,983 disclose aqueous-coatable DRL formulations based on poly (vinyl alcohol). Iqbal in U.S. Pat. No. 5,208,092 discloses water-based IRL (ink receiving layer) formulations comprising vinyl copolymers which are subsequently cross-linked. In addition to these examples, there may be other known or contemplated DRL formulations which are consistent with the aforementioned primary and secondary requirements of the DRL, all of which fall under the spirit and scope of the current invention.

The preferred DRL is a 0.1–10 micrometers DRL which is coated as an aqueous dispersion of 5 parts alumoxane and 5 parts poly (vinyl pyrrolidone). The DRL may also contain varying levels and sizes of matting agents for the purpose of controlling gloss, friction, and/or fingerprint resistance, surfactants to enhance surface uniformity and to adjust the surface tension of the dried coating, mordanting agents, antioxidants, UV absorbing compounds, light stabilizers, and the like.

Although the ink-receiving elements as described above can be successfully used to achieve the objectives of the present invention, it may be desirable to overcoat the DRL for the purpose of enhancing the durability of the imaged element. Such overcoats may be applied to the DRL either before or after the element is imaged. For example, the DRL can be overcoated with an ink-permeable layer through which inks freely pass. Layers of this type are described in U.S. Pat. Nos. 4,686,118; 5,027,131; and 5,102,717. Alternatively, an overcoat may be added after the element is imaged. Any of the known laminating films and equipment may be used for this purpose. The inks used in the aforementioned imaging process are well known, and the ink formulations are often closely tied to the specific processes, i.e., continuous, piezoelectric, or thermal. Therefore, depending on the specific ink process, the inks may contain widely differing amounts and combinations of solvents, colorants, preservatives, surfactants, humectants, and the like. Inks preferred for use in combination with the image recording elements of the present invention are water-based, such as those currently sold for use in the Hewlett-Packard Desk Writer 560C printer. However, it is intended that alternative embodiments of the image-recording elements as described above, which may be formulated for use with inks which are specific to a given ink-recording process or to a given commercial vendor, fall within the scope of the present invention.

An image recording element for ink jet printing comprises a base layer and an image receiving layer coated onto a base consisting of a strength layer and a heat shrinkable sheet. For the base layer, a mixture of 60% by weight lime-process ossein photographic grade gelatin, 30% by weight of polyvinylpyrrolidone (PVP K-90, ISP) and 10% by weight of Mordant 1 was prepared. Mordant 1 consists of a polymer prepared from (vinylbenzyl)trimethylammonium chloride and divinylbenzene as described in U.S. Pat. No. 6,045,917 of Missell et al. The pH of the mixture was adjusted to 3.5 by addition of hydrochloric acid (36–38%, J T Baker). Some surfactant (Dixie 10G, Dixie Chemicals) was added to enhance coatability. A 10% coating solution of the mixture was prepared and slot coated onto the support and dried at 100° C. to give a dry coverage of 5.4 g/$m^2$.

For the image receiving layer, a mixture of 80% by weight of hydroxyethyl cellulose (Quatrisoft® LM200, Amerchol) and 20% by weight of methyl cellulose (Methocel® A4M, Dow Chemical) was prepared. Surfactants (Dixie® 10G, Dixie Chemicals and Zonyl® FSN, DuPont) were added to enhance coatability. A 2% coating solution of the mixture was prepared and slot coated onto the base layer and dried at 100° C. to give a dry coverage of 1.1 g/$m^2$.

The preferred photographic element of this invention is directed to a silver halide photographic element capable of excellent performance when exposed by either an electronic printing method or a conventional optical printing method. An electronic printing method comprises subjecting a radiation sensitive silver halide emulsion layer of a recording element to actinic radiation of at least $10^{-4}$ ergs/$cm^2$ for up to 100$\mu$ seconds duration in a pixel-by-pixel mode wherein the silver halide emulsion layer is comprised of silver halide grains as described above. A conventional optical printing method comprises subjecting a radiation sensitive silver halide emulsion layer of a recording element to actinic radiation of at least $10^{-4}$ ergs/$cm^2$ for $10^{-3}$ to 300 seconds in an imagewise mode wherein the silver halide emulsion layer is comprised of silver halide grains as described above. This invention in a preferred embodiment utilizes a radiation-sensitive emulsion comprised of silver halide grains (a) containing greater than 50 mole percent chloride based on silver, (b) having greater than 50 percent of their surface area provided by {100} crystal faces, and (c) having a central portion accounting for from 95 to 99 percent of total silver and containing two dopants selected to satisfy each of the following class requirements: (i) a hexacoordination metal complex which satisfies the formula:

$$[ML_6]^n \qquad (I)$$

wherein n is zero, −1, −2, −3, or −4; M is a filled frontier orbital polyvalent metal ion, other than iridium; and $L_6$ represents bridging ligands which can be independently selected, provided that at least four of the ligands are anionic ligands, and at least one of the ligands is a cyano ligand or a ligand more electronegative than a cyano ligand; and (ii) an iridium coordination complex containing a thiazole or substituted thiazole ligand. Preferred photographic imaging layer structures are described in EP Publication 1 048 977. The photosensitive imaging layers described therein provide particularly desirable images on the pragmatic sheet of this invention.

The invention has been described in detail with particular reference to certain preferred embodiments thereof, but it will be understood that variations and modifications can be effected within the spirit and scope of the invention.

EXAMPLES

The polymers used in the example environmental protection layers were obtained commercially. The acrylic urethane hybrid polymer, SancureAU4010 was obtained from BF Goodrich. The urethane polymer NeoRez R600 was obtained from NeoResins (a division of Avecia). The crosslinker CX100 (polyfunctional aziridene), for the environmental protection layer polymers was obtained from NeoResins (a division of Avecia). The lubricant EXP-42-LS, a silicone wax emulsion copolymer was obtained from Genesee Polymers Corporation.

Porous beads used for encapsulating lavender oil was prepared by forming a suspension or dispersion of ethylene glycol dimethacrylate monomer droplets containing 35% by weight toluene as a porogen in an aqueous medium, polymerizing the monomer to form solid, porous polymeric particles in the presence of an anionic surfactant, and removing the toluene by vacuum stripping as described in U.S. Pat. No. 09/608,466 filed Jun. 30, 2000. The particles thus prepared had a nominal particle size of 0.16 micrometers. Lavender oil was loaded into the porous particles at 35 weight percent by stirring the beads with the oil for 18 hours. Musk ambrette, a solid fragrance was loaded in another batch of the porous particles by stirring the musk dissolved in ethyl acetate (as a 10% solution) for 18 hours followed by evaporation of the solvent using a rotary evaporator under reduced pressure.

Example 1

The environmental protection layer containing an encapsulated scent was coated over a silver halide imaged and processed label using the formulation and architecture described below.

A silver halide pressure sensitive packaging label was created by applying a light sensitive silver halide imaging layers to a pressure sensitive label stock. The label stock consisted of a flexible white biaxially oriented polypropylene face stock coated with a pressure sensitive adhesive that was laminated to a high strength polyester liner. The light sensitive silver halide imaging layers were a yellow, magenta, and cyan coupler system capable of accurate reproduction of flesh tone. This label stock was imaged and processed prior to overcoating with the environmental protection layer.

Biaxially Oriented Polyolefin Face Stock

A composite sheet polyolefin sheet (31 μm thick) (d=0.68 g/cc) consisting of a microvoided and oriented polypropylene core (approximately 60% of the total sheet thickness), with a homopolymer non-microvoided oriented polypropylene layer on each side of the voided layer; the void initiating material used was poly(butylene terephthalate). The polyolefin sheet had a skin layer consisting of polyethylene and a blue pigment. The polypropylene layer adjacent the voided layer contained 4% rutile $TiO_2$ and optical brightener. The silver halide imaging layers were applied to the blue tinted polyethylene skin layer.

Pressure Sensitive Adhesive

Permanent water based acrylic adhesive 12 μm thick

Polyester Liner

A polyethylene terephthalate liner 37 μm thick that was transparent. The polyethylene terephthalate base had a stiffness of 15 millinewtons in the machine direction and 20 millinewtons in the cross direction.

Structure of the Base and Liner for the Photographic Packaging Label Material of the Example is as Follows:

Voided polypropylene sheet
Acrylic pressure sensitive adhesive
Polyester liner

Silver chloride emulsions were chemically and spectrally sensitized as described below. A biocide comprising a mixture of N-methyl-isothiazolone and N-methyl-5-chloro-isthiazolone was added after sensitization.

Blue Sensitive Emulsion (Blue EM-1)

A high chloride silver halide emulsion is precipitated by adding approximately equimolar silver nitrate and sodium chloride solutions into a well-stirred reactor containing glutaryldiaminophenyldisulfide, gelatin peptizer, and thioether ripener. Cesium pentachloronitrosylosmate(II) dopant is added during the silver halide grain formation for most of the precipitation, followed by the addition of potassium hexacyanoruthenate(II), potassium (5-methyl-thiazole)-pentachloroiridate, a small amount of KI solution, and shelling without any dopant. The resultant emulsion contains cubic-shaped grains having edge length of 0.6 μm. The emulsion is optimally sensitized by the addition of a colloidal suspension of aurous sulfide and heat ramped to 60° C., during which time blue sensitizing dye BSD-4, potassium hexchloroiridate, Lippmann bromide, and 1-(3-acetamidophenyl)-5-mercaptotetrazole were added.

Green Sensitive Emulsion (Green EM-1)

A high chloride silver halide emulsion is precipitated by adding approximately equimolar silver nitrate and sodium chloride solutions into a well-stirred reactor containing gelatin peptizer and thioether ripener. Cesium pentachloronitrosylosmate(II) dopant is added during the silver halide grain formation for most of the precipitation, followed by the addition of potassium (5-methylthiazole)-pentachloroiridate. The resultant emulsion contains cubic-shaped grains of 0.3 μm in edge length size. The emulsion is optimally sensitized by the addition of glutaryldiaminophenyldisulfide, a colloidal suspension of aurous sulfide and heat ramped to 55° C., during which time potassium hexachloroiridate doped Lippmann bromide, a liquid crystalline suspension of green sensitizing dye GSD-1, and 1-(3-acetamidophenyl)-5-mercaptotetrazole were added.

Red Sensitive Emulsion (Red EM-1)

A high chloride silver halide emulsion is precipitated by adding approximately equimolar silver nitrate and sodium chloride solutions into a well-stirred reactor containing gelatin peptizer and thioether ripener. During the silver halide grain formation, potassium hexacyanoruthenate(II) and potassium (5-methylthiazole)-pentachloroiridate are added. The resultant emulsion contains cubic shaped grains of 0.4 μm in edge length size. The emulsion is optimally sensitized by the addition of glutaryldiaminophenyldisulfide, sodium thiosulfate, tripotassium bis {2-[3-(2-sulfobenzamido)phenyl]-mercaptotetrazole} gold(I) and heat ramped to 64° C., during which time 1-(3-acetamidophenyl)-5-mercaptotetrazole, potassium hexachloroiridate, and potassium bromide are added. The emulsion is then cooled to 40° C., pH adjusted to 6.0, and red sensitizing dye RSD-1 is added.

Coupler dispersions were emulsified by methods well known to the art, and the following layers were coated on the following support:

The following flesh tone optimized light sensitive silver halide imaging layers were utilized to prepare photographic label utilizing the invention label base material. The following imaging layers were coated utilizing curtain coating. The gelatin containing layers were hardened with bis (vinylsulfonyl methyl) ether at 1.95% of the total gelatin weight.

TABLE 1

| Layer | Item | Laydown ($g/m^2$) |
|---|---|---|
| Layer 1 | Blue Sensitive Layer | |
| | Gelatin | 1.3127 |
| | Blue sensitive silver (Blue EM-1) | 0.2399 |
| | Y-4 | 0.4143 |
| | ST-23 | 0.4842 |
| | Tributyl Citrate | 0.2179 |
| | ST-24 | 0.1211 |
| | ST-16 | 0.0095 |
| | Sodium Phenylmercaptotetrazole | 0.0001 |
| | Piperidino hexose reductone | 0.0024 |
| | 5-chloro-2-methyl-4-isothiazolin-3-one/2-methyl-4-isothiazolin-3-one(3/1) | 0.0002 |
| | SF-1 | 0.0366 |
| | Potassium chloride | 0.0204 |
| | Dye-1 | 0.0148 |

TABLE 1-continued

| Layer | Item | Laydown ($g/m^2$) |
|---|---|---|
| Layer 2 | Interlayer | |
| | Gelatin | 0.7532 |
| | ST-4 | 0.1076 |
| | S-3 | 0.1969 |
| | 5-chloro-2-methyl-4-isothiazolin-3-one/2-methyl-4-isothiazolin-3-one(3/1) | 0.0001 |
| | Catechol disulfonate | 0.0323 |
| | SF-1 | 0.0081 |
| Layer 3 | Green Sensitive Layer | |
| | Gelatin | 1.1944 |
| | Green sensitive silver (Green EM-1) | 0.1011 |
| | M-4 | 0.2077 |
| | Oleyl Alcohol | 0.2174 |
| | S-3 | 0.1119 |
| | ST-21 | 0.0398 |
| | ST-22 | 0.2841 |
| | Dye-2 | 0.0073 |
| | 5-chloro-2-methyl-4-isothiazolin-3-one/2-methyl-4-isothiazolin-3-one(3/1) | 0.0001 |
| | SF-1 | 0.0236 |
| | Potassium chloride | 0.0204 |
| | Sodium Phenylmercaptotetrazole | 0.0007 |
| Layer 4 | M/C InterLayer | |
| | Gelatin | 0.7532 |
| | ST-4 | 0.1076 |
| | S-3 | 0.1969 |
| | Acrylamide/t-Butylacrylamide sulfonate copolymer | 0.0541 |
| | Bis-vinylsulfonylmethane | 0.1390 |
| | 3,5-Dinitrobenzoic acid | 0.0001 |
| | Citric acid | 0.0007 |
| | Catechol disulfonate | 0.0323 |
| | 5-chloro-2-methyl-4-isothiazolin-3-one/2-methyl-4-isothiazolin-3-one(3/1) | 0.0001 |
| Layer 5 | Red Sensitive Layer | |
| | Gelatin | 1.3558 |
| | Red Sensitive silver (Red EM-1) | 0.1883 |
| | IC-35 | 0.2324 |
| | IC-36 | 0.0258 |
| | UV-2 | 0.3551 |
| | Dibutyl sebacate | 0.4358 |
| | S-6 | 0.1453 |
| | Dye-3 | 0.0229 |
| | Potassium p-toluenethiosulfonate | 0.0026 |
| | 5-chloro-2-methyl-4-isothiazolin-3-one/2-methyl-4-isothiazoiin-3-one(3/1) | 0.0001 |
| | Sodium Phenylmercaptotetrazole | 0.0005 |
| | SF-1 | 0.0524 |
| Layer 6 | UV Overcoat | |
| | Gelatin | 0.8231 |
| | UV-1 | 0.0355 |
| | UV-2 | 0.2034 |
| | ST-4 | 0.0655 |
| | SF-1 | 0.0125 |
| | S-6 | 0.0797 |
| | 5-chloro-2-methyl-4-isothiazolin-3-one/2-methyl-4-isothiazolin-3-one(3/1) | 0.0001 |
| Layer 7 | SOC | |
| | Gelatin | 0.6456 |
| | Ludox AM ™ (colloidal silica) | 0.1614 |
| | Polydimethylsiloxane (DC200 ™ ) | 0.0202 |
| | 5-chloro-2-methyl-4-isothiazolin-3-one/2-methyl-4-isothiazolin-3-one(3/1) | 0.0001 |
| | SF-2 | 0.0032 |
| | Tergitol 15-S-5 ™ (surfactant) | 0.0020 |
| | SF-1 | 0.0081 |
| | Aerosol OT ™ (surfactant) | 0.0029 |

The rolls of light sensitive silver halide emulsion coated on the label support of this example were printed using a digital CRT photographic printer. Several test images that contained graphics, text, and images were printed on the photographic packaging label material. The printed images were then developed using standard reflective photographic RA 4 wet chemistry. At this point, the image was formed on a thin label support. The environmental protection layers of the invention were applied using extrusion hopper coating from a coating solution at 13 weight percent solids over the topmost gelatin layer of the imaging layers.

The structure of the imaged, protected silver halide pressure sensitive packaging label was as follows:

Environmental protection layer
Developed silver halide imaging layers (yellow, magenta and cyan)
Voided polypropylene sheet
Acrylic pressure sensitive adhesive
Polyester liner A vinyl polymer Sancure AU 4010 (acrylic-urethane hybrid polymer) was coated as a mixture with a urethane polymer NeoRez R600 as the environmental protection layer. Sancure AU 4010 was present at 50 weight percent of the total polymer in the layer. The dry coverage of the polymer mixture was 2.15g/$m^2$. Lavender loaded porous beads described earlier were added to the coating solution at 4.5 weight percent beads with respect to total polymer prior to coating. This resulted in a dry coverage of 0.03 g/$m^2$ of lavender oil in the environmental protection layer. The polymer layer was crosslinked with 3 weight percent CX100 with respect to the total polymer in the layer. The layer also contained 0.43 g/$m^2$ of EXP-24-LS lubricant. The clear glossy dried coating had a lavender smell which was enhanced upon rubbing the coating with a finger.

Example 2

A solid fragrance, musk ambrette, was incorporated in the environmental protection layer as described above except that in place of lavender loaded porous beads were used. The clear glossy coating had a long lasting distinct smell of musk.

Appendix—Compounds Used in Examples

BSD-4

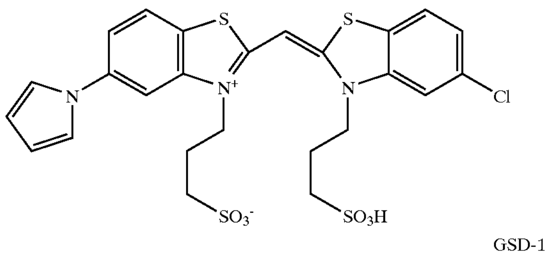

GSD-1

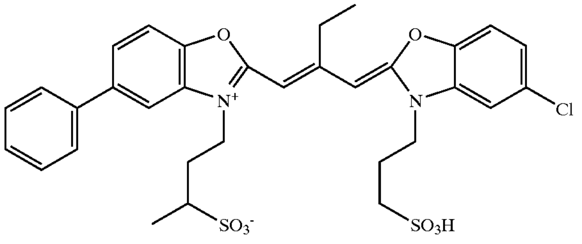

-continued
RSD-1
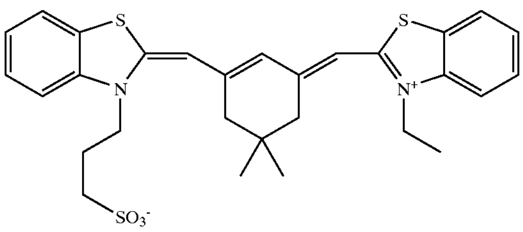
Y-4
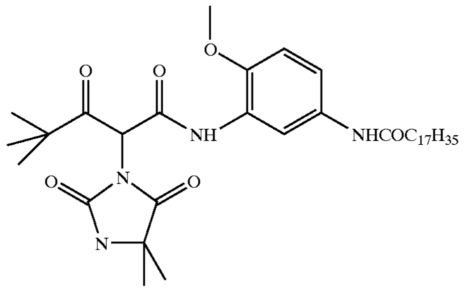
ST-23
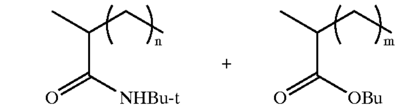
ST-24
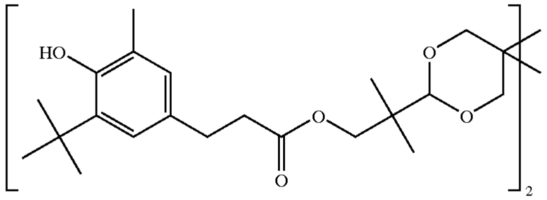
ST-16
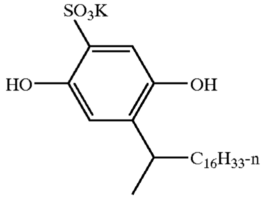
SF-1
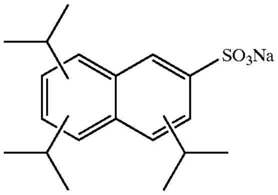
Dye-1
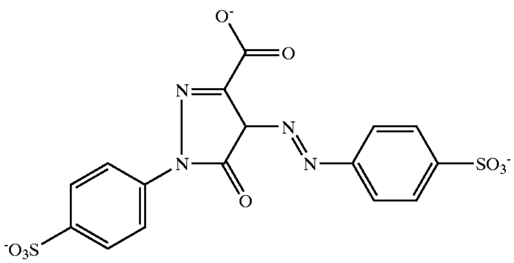
-continued
ST-4
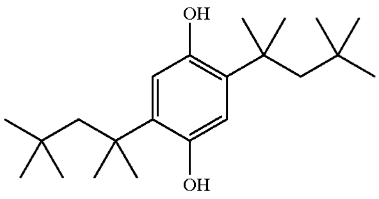
S-3
Diudecyl phthalate
M-4
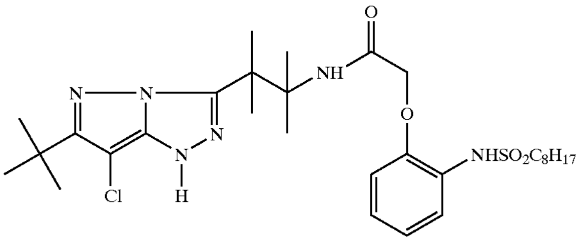
ST-21
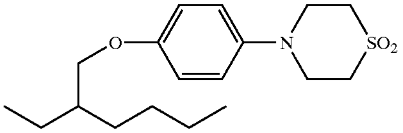
ST-22
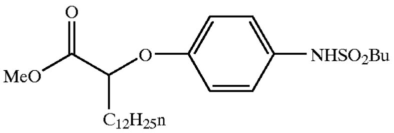
Dye-2
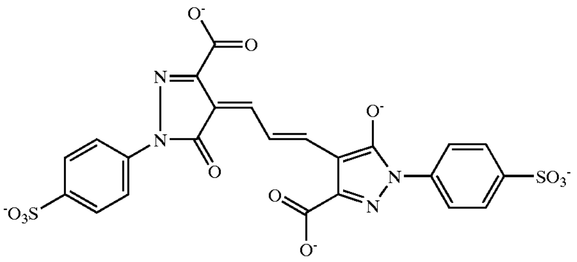
IC-35
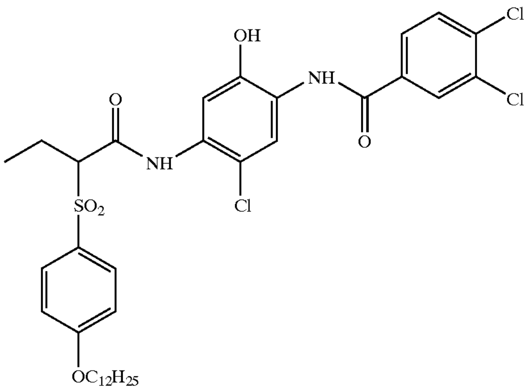

-continued

IC-36

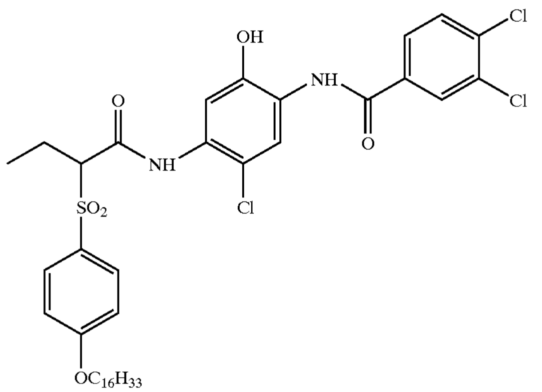

S-6

Tris(2-ethylhexyl)phosphate

Dye-3

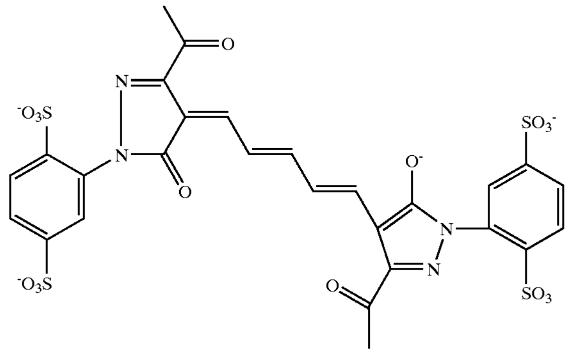

UV-1

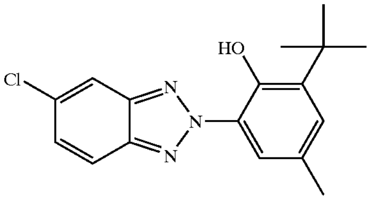

UV-2

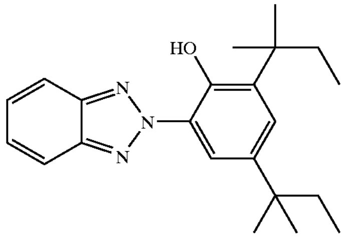

The invention has been described in detail with particular reference to certain preferred embodiments thereof, but it will be understood that variations and modifications can be effected within the spirit and scope of the invention.

What is claimed is:

1. A sensual pressure sensitive adhesive label comprising an image having at least one overcoat layer over said image wherein said overcoat layer comprises at least one tactile or olfactory feature wherein said overcoat layer comprises a mixture of vinyl polymer and urethane polymer wherein said urethane polymer has an indentation modulus less than 0.6 GPa and wherein said overcoat layer is less than 10 micrometers in thickness.

2. The label of claim 1 wherein said feature comprises a pressure-releasable scent.

3. The label of claim 2 wherein said pressure-releasable scent is released by microsponges.

4. The label of claim 1 wherein said feature comprises pressure release of a liquid.

5. The label of claim 2 wherein said liquid comprises an oil-based material.

6. The label of claim 2 wherein said pressure-releasable scent is released from particles in which it is encapsulated.

7. The label of claim 5 wherein said pressure-releasable oil-based material is encapsulated in fragrances.

8. The label of claim 1 wherein said at least one overcoat layer comprises a textured surface.

9. The label of claim 8 wherein said textured surface comprises only a portion of said overcoat layer.

10. The label of claim 8 wherein said textured surface comprises particles.

11. The image element of claim 10 wherein said particles have an average particle size of between 2 μm to 500 μm.

12. The image element of claim 11 wherein said particles have an average particle size of between 2 μm to 100 μm.

13. The image element of claim 8 wherein said textured surface has a depth of between 5 μm to 100 μm.

14. The image element of claim 8 wherein said textured surface comprises braille indicia.

15. The image element of claim 1 wherein said image element has at least one partial layer overlaying an overcoat layer that comprises an olfactory barrier layer, the overcoat layer comprises an olfactory feature.

16. The image element of claim 8 wherein said textured surface is in a pattern.

17. The image element of claim 8 wherein said textured surface is in intermittent areas.

18. The image element of claim 2 wherein said pressure-releasable scent overlays specific areas of said image.

19. The image element of claim 18 wherein said feature location corresponds to a complimentary area of said image.

20. The image element of claim 1 wherein said at least one overlaying layer comprises both olfactory and sensory features.

21. The image element of claim 1 wherein said image layer is on a base that has a lower pressure sensitive adhesive layer.

22. The image element of claim 1 wherein said image comprises an image formed by photosensitive silver halide.

23. The image element of claim 1 wherein said at least one tactile or olfactory feature comprises a tactile feature.

24. The image element of claim 23 wherein said image comprises a thermal transfer dye image.

25. The method comprising providing an image and overcoating said image with at least one layer comprising a sensory or olfactory feature wherein said overcoat layer comprises a mixture of vinyl polymer and urethane polymer wherein said urethane polymer has an indentation modulus less than 0.6 GPa and wherein said overcoat layer is less than 10 micrometers in thickness.

26. The method of claim 25 said feature comprises a pressure-releasable scent.

27. The method of claim 26 wherein said pressure releasable scent is released by microsponges.

28. The method of claim 25 wherein said feature comprises pressure release of a liquid.

29. The method of claim 28 wherein said liquid comprises an oil-based material.

30. The method of claim 26 wherein said pressure releasable scent is released from particles.

31. The method of claim 25 wherein said image is on a base that has a lower pressure sensitive adhesive layer.

32. The method of claim 25 wherein said image comprises an image formed by photosensitive silver halide.

33. The method of claim 25 wherein said overcoat layer is coated using gravure coating.

34. The method of claim 25 wherein said overcoat layer comprises a ultraviolet radiation cured environmental protection layer and a primer layer.

35. The method of claim 25 wherein said overcoat layer is discontinuous such that a fraction of the surface area of the image element remains uncovered by said overcoat layer.

36. The method comprising providing an image and overcoating said image with at least one layer comprising a sensory or olfactory feature, wherein said overcoat layer comprises a ultraviolet radiation cured environmental protection layer and a primer layer.

37. The method of claim 36 said feature comprises a pressure-releasable scent.

38. The method of claim 37 wherein said pressure releasable scent is released by microsponges.

39. The method of claim 37 wherein said pressure releasable scent is released from particles.

40. The method of claim 36 wherein said image is on a base that has a lower pressure sensitive adhesive layer.

41. The method of claim 37 wherein said overcoat layer comprises a mixture of vinyl polymer and urethane polymer wherein said urethane polymer has an indentation modulus less than 0.6 GPa and wherein said overcoat layer is less than 10 micrometers in thickness.

42. The method of claim 36 wherein said overcoat layer is discontinuous such that a fraction of the surface area of the image element remains uncovered by said overcoat layer.

43. A sensual pressure sensitive adhesive label comprising an image having at least one overcoat layer over said image wherein said overcoat layer comprises at least one tactile or olfactory feature, wherein said overcoat layer comprises a ultraviolet radiation cured environmental protection layer and a primer layer.

44. The label of claim 43 wherein said feature comprises a pressure-releasable scent.

45. The label of claim 43 wherein said feature comprises pressure release of a liquid.

46. The label of claim 44 wherein said pressure-releasable scent is released from particles in which it is encapsulated.

47. The label of claim 44 wherein said at least one overcoat layer comprises a textured surface.

48. The label of claim 47 wherein said textured surface comprises only a portion of said overcoat layer.

49. The label of claim 47 wherein said textured surface comprises particles.

50. The image element of claim 47 wherein said textured surface has a depth of between 5 $\mu$m to 100 $\mu$m.

51. The image element of claim 47 wherein said textured surface is in a pattern.

52. The image element of claim 43 wherein said at least one overlaying layer comprises both olfactory and sensory features.

53. The image element of claim 43 wherein said image layer is on a base that has a lower pressure sensitive adhesive layer.

* * * * *